US011220708B2

(12) United States Patent
Judice

(10) Patent No.: US 11,220,708 B2
(45) Date of Patent: *Jan. 11, 2022

(54) COMPOSITIONS AND METHODS FOR DETECTING NICKING ENZYME AND POLYMERASE ACTIVITY USING A SUBSTRATE MOLECULE

(71) Applicant: ENVIROLOGIX INC., Portland, ME (US)

(72) Inventor: Stephen A. Judice, Portland, ME (US)

(73) Assignee: ENVIROLOGIX INC., Portland, ME (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/782,838

(22) Filed: Feb. 5, 2020

(65) Prior Publication Data

US 2020/0157612 A1    May 21, 2020

Related U.S. Application Data

(63) Continuation of application No. 15/546,582, filed as application No. PCT/US2016/014753 on Jan. 25, 2016, now Pat. No. 10,570,441.

(60) Provisional application No. 62/110,237, filed on Jan. 30, 2015.

(51) Int. Cl.
| | |
|---|---|
| *C12P 19/34* | (2006.01) |
| *C12Q 1/6818* | (2018.01) |
| *C12Q 1/6823* | (2018.01) |
| *C07H 21/00* | (2006.01) |
| *C07H 21/04* | (2006.01) |

(52) U.S. Cl.
CPC ........... *C12Q 1/6818* (2013.01); *C07H 21/00* (2013.01); *C07H 21/04* (2013.01); *C12P 19/34* (2013.01); *C12Q 1/6823* (2013.01); *C12Y 207/07* (2013.01); *C12Y 301/00* (2013.01)

(58) Field of Classification Search
CPC .................................................. C12Q 1/6818
See application file for complete search history.

(56) References Cited

U.S. PATENT DOCUMENTS

| 7,112,423 B2 | 9/2006 | Van Ness et al. |
| 7,282,328 B2 | 10/2007 | Kong et al. |
| 10,570,441 B2 | 2/2020 | Judice |
| 2009/0081670 A1 | 3/2009 | Maples et al. |
| 2013/0280706 A1 | 10/2013 | Judice |
| 2015/0104788 A1 | 4/2015 | Shaffer et al. |
| 2018/0037940 A1 | 2/2018 | Judice |

FOREIGN PATENT DOCUMENTS

| CN | 101952459 A | 1/2011 |
| JP | 2010533494 A | 10/2010 |
| WO | 2006088911 A2 | 8/2006 |
| WO | 2009012246 A2 | 1/2009 |
| WO | 2010120853 A2 | 10/2010 |
| WO | 2012021493 A2 | 2/2012 |
| WO | 2013040992 A1 | 3/2013 |
| WO | 2013155056 A1 | 10/2013 |
| WO | 2014161975 A1 | 10/2014 |

OTHER PUBLICATIONS

Search Report received in corresponding Chinese Patent Application No. 201680020115.4, dated Aug. 13, 2020 (3 pages).
Office Action received in corresponding Chinese Patent Application No. 201680020115.4, dated Aug. 19, 2020 (11 pages).
English explanation of the Office Action received in corresponding Chinese Patent Application No. 201680020115.4, dated Aug. 19, 2020 (18 pages).
Office Action received in corresponding Ukrainian Patent Application No. a201708718, dated Sep. 18, 2020 (4 pages).
English translation of the Office Action received in corresponding Ukrainian Patent Application No. a201708718, dated Sep. 18, 2020 (3 pages).
Extended European Search Report in corresponding European Patent Application No. 16743914.0, dated Sep. 20, 2018 (9 pages).
International Search Report and Written Opinion in corresponding PCT Patent Application No. PCT/US2016/014753, dated Jul. 12, 2016 (13 pages).
Brazilian Office Action in corresponding Brazilian Patent Application No. BR 112017016350-0, dated Dec. 18, 2019 (4 pages).
English explanation of Brazilian Office Action in corresponding Brazilian Patent Application No. BR 112017016350-0, dated Dec. 18, 2019 (2 pages).
Russian Office Action in corresponding Russian Patent Application No. 2017130477, dated Aug. 7, 2019 (3 pages).
English translation of Russian Office Action in corresponding Russian Patent Application No. 2017130477, dated Aug. 7, 2019 (3 pages).
Russian Office Action in corresponding Russian Patent Application No. 2017130477, dated Nov. 25, 2019 (4 pages).
English translation of Russian Office Action in corresponding Russian Patent Application No. 2017130477, dated Nov. 25, 2019 (4 pages).
Office Action received in corresponding Japanese Patent Application No. 2017-540627, dated Nov. 9, 2020 (2 pages).
English translation of the Office Action received in corresponding Japanese Patent Application No. 2017-540627, dated Nov. 9, 2020 (2 pages).
Office Action issued in corresponding Argentina Patent Application No. 20160100275, dated Jul. 7, 2020 (4 pages).
English explanation of the Office Action issued in corresponding Argentina Patent Application No. 20160100275, dated Jul. 7, 2020 (3 pages).

(Continued)

*Primary Examiner* — Kenneth R Horlick
(74) *Attorney, Agent, or Firm* — Melissa Hunter-Ensor; Nicholas R. Ballor; Greenberg Traurig, LLP

(57) ABSTRACT

The present invention provides compositions and methods for assaying the activity of nicking enzyme and polymerase in a reaction involving the use of a nucleic acid substrate molecule that detects nicking enzyme and polymerase extension activities by the release of a detectable reporter (e.g., a fluorophore).

30 Claims, 16 Drawing Sheets

Specification includes a Sequence Listing.

(56) References Cited

OTHER PUBLICATIONS

Office Action in corresponding Japanese Patent Application No. 2017-540627, dated Feb. 17, 2020 (3 pages).
English Translation of Office Action in corresponding Japanese Patent Application No. 2017-540627, dated Feb. 17, 2020 (3 pages).
Office Action dated Jul. 7, 2021 in corresponding Chinese Patent Application No. 201680020115.4 (5 pages).
English translation of the Office Action dated Jul. 7, 2021 in corresponding Chinese Patent Application No. 201680020115.4 (5 pages).

FIG. 1A

Generalized Dual enzyme activity reaction control

▬ = GAGTC
▨ = Nick site

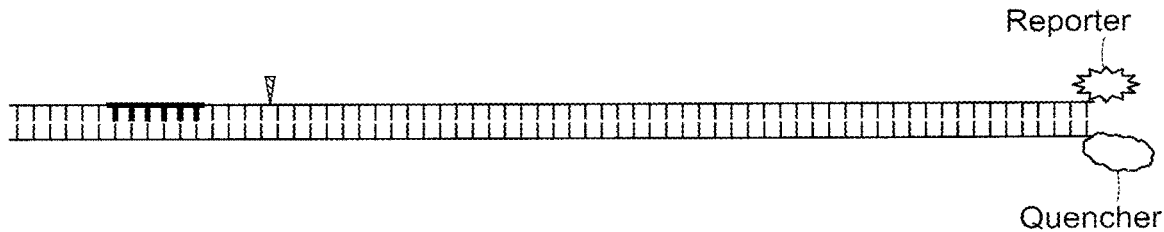

FIG. 1B

Oligonucleotide duplex with one oligo labeled with a fluorophore on one end and the other oligo with a quencher on the opposite end leading to a quenched fluorescent signal when annealed. I.e. A 3' Fam label and a 5' quencher (of fret molecule such as Hex).

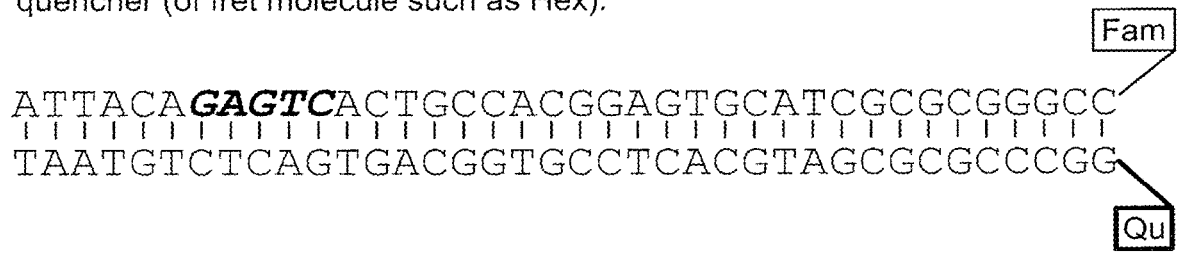

FIG. 1C

Duplexed oligonucleotide is nicked by nicking enzyme

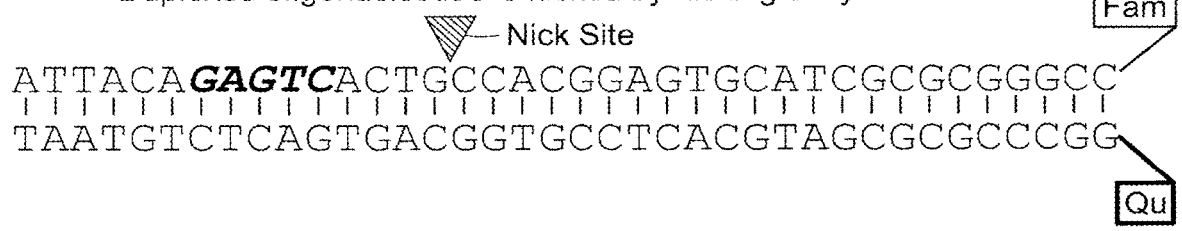

FIG. 1D

Polymerase contacts at nicksite

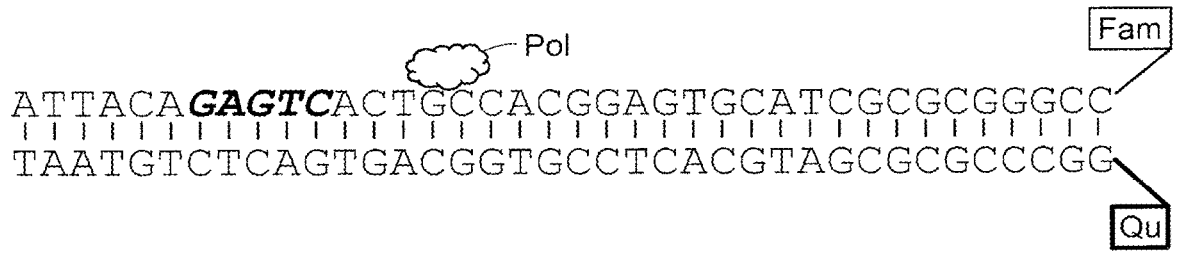

FIG. 1E

Polymerase extends off 3' end to displace the top strand 3' of the nicksite, allowing the reporter dye to fluoresce.

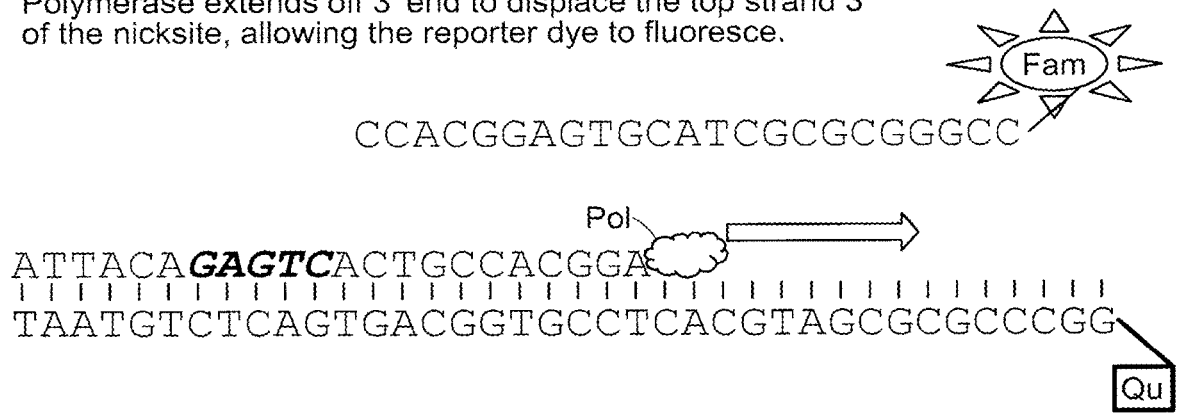

FIG. 1F

Molecule can be nicked again. This can lead to additional generated 'shortmers' which through their design can be made to self-bind and 'closeout' the reaction. Additionally, the sequence of the region 5' of the nicksite can be designed to be unstable at the reaction temperature such that it can fall off, preventing extension from the free 3' end.

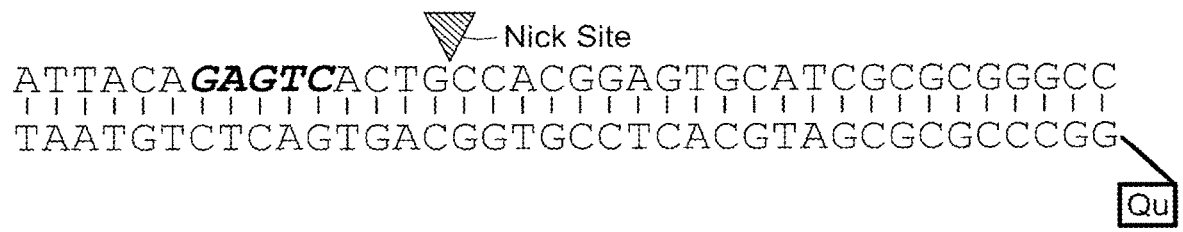

- The reaction creates a linear rise in signal with 3' blocked oligos (blocked by either a fluorophore or some other blocking molecule such as a C3 spacer).

Reaction end points can be determined by the time at which the exogenous control reaches a set RFU

FIG. 3A
Generalized Dual enzyme activity 'longmer'
- Multiple reporters (can be different colors to indicate processivity of polymerase).
- One quencher for each reporter.
- dsDNA molecule up to 2000bp.
- May contain base modifications, adducts, etc to investigate the effect of these modifications on enzyme processivity.

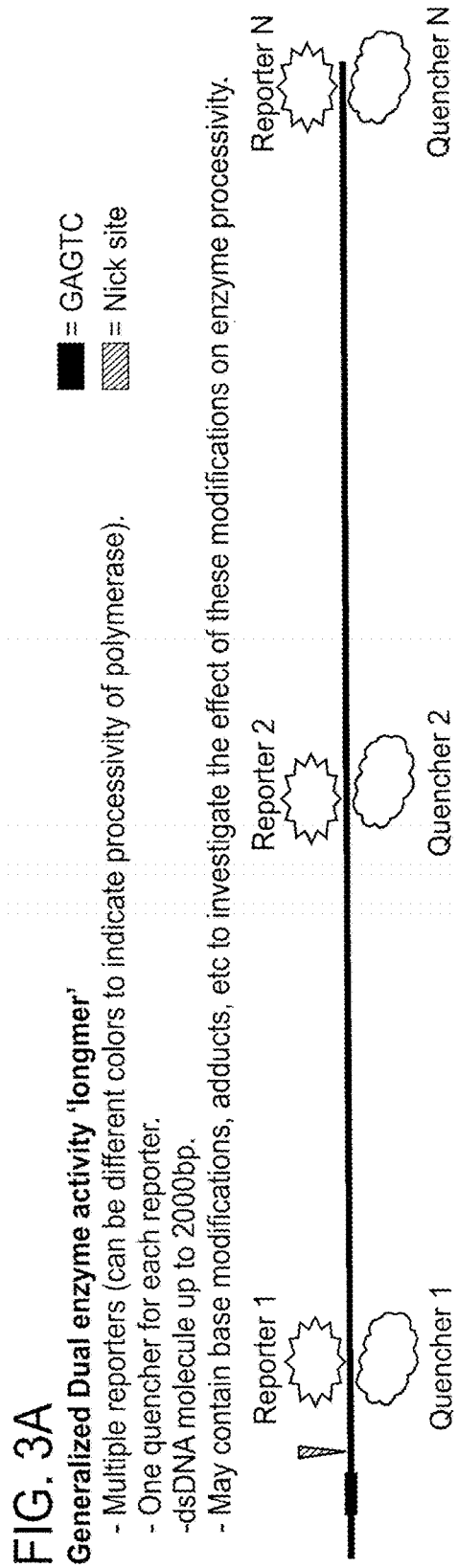

FIG. 3B
Utility of the 'Longmer' version includes but is not limited to investigations of:
- Processivity of polymerase on DNA template to assess polymerase activity (i.e. for a QC in manufacture).
- DNA methylation: DNA methylation sites are typically on the cytosine of CpG sites at the C5 position (5-methylcytosine).

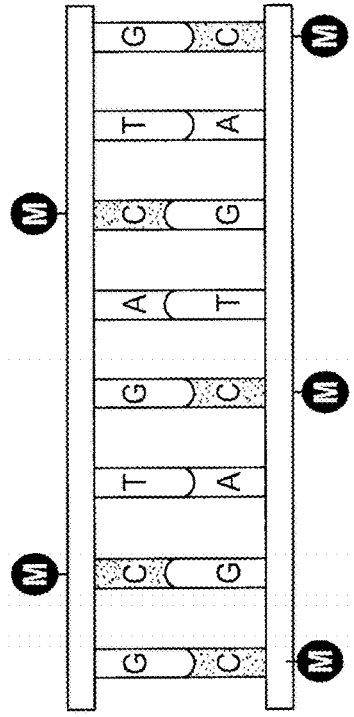

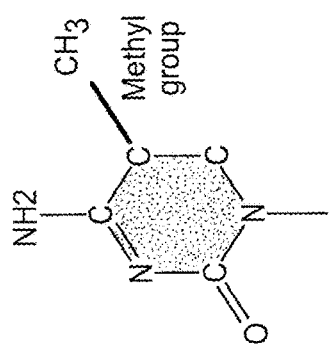

- DNA adducts/damage products: examples include acetaldehyde, cisplatin, 7,12-dimethylbenzanthracene, malondialdehyde, products of base excision repair, oxidative damage products, benzopyrene, aflatoxin, other DNA reactive compounds.
- DNA binding proteins.

FIG. 4

| | | |
|---|---|---|
| ExogContBOT | 38 | /5IAbRQ/GGCCCGGCGGATGCACTCCGTGGCAGTGACTCTGTAAT |
| Vanilla | 38 | ATTACAGAGTCACTGCCACGGAGTGCATCGCGGGGCC/36-FAM/ |
| Nick -2 | 38 | ATTACAGAGTCACmUGCCCACGGAGTGCATCGCGGGGCC/36-FAM/ |
| Nick +1 | 38 | ATTACAGAGTCACTGmCCACGGAGTGCATCGCGGGGCC/36-FAM/ |
| Nick -1 | 38 | ATTACAGAGTCACTmGCCACGGAGTGCATCGCGGGGCC/36-FAM/ |

FIG. 7

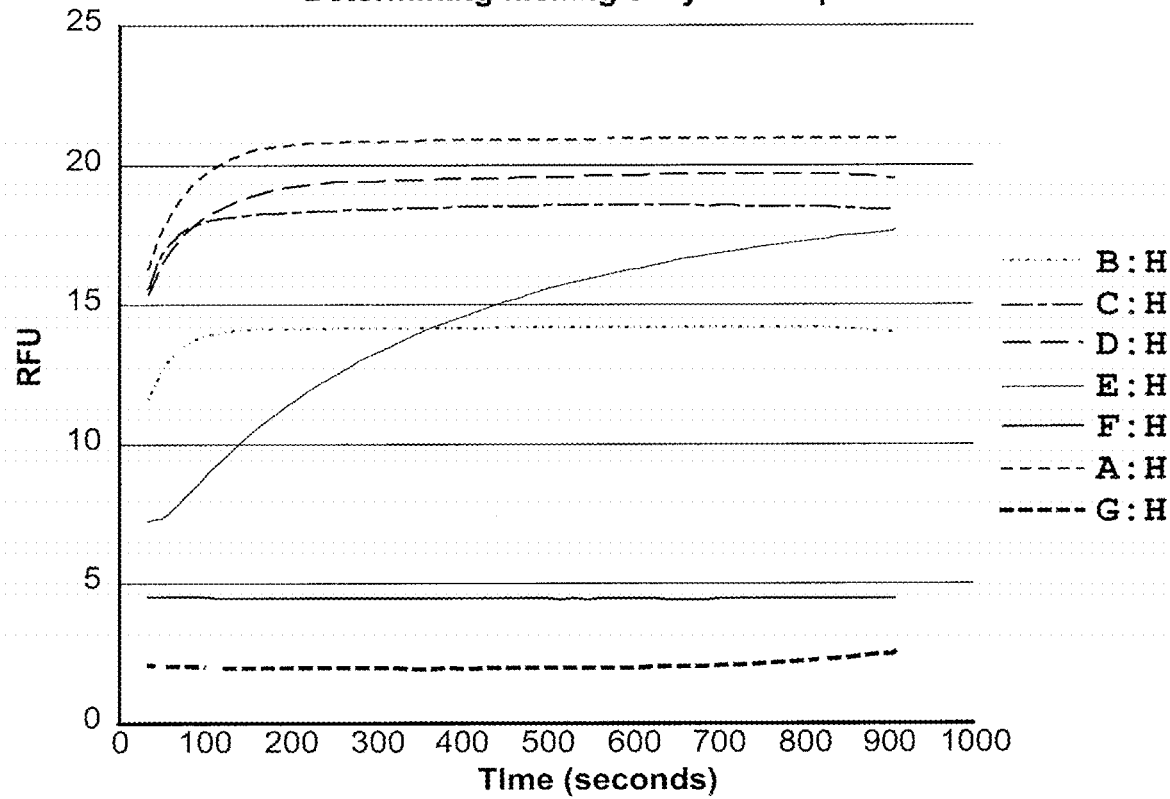

| A | ATTACA*GAGTC*ACTGCCACGGAGTGCATCGCGCGGGCC/36-FAM/ |
| B | TACA*GAGTC*ACTGCCACGGAGTGCATCGCGCGGGCC/36-FAM/ |
| C | ACA*GAGTC*ACTGCCACGGAGTGCATCGCGCGGGCC/36-FAM/ |
| D | CA*GAGTC*ACTGCCACGGAGTGCATCGCGCGGGCC/36-FAM/ |
| E | A*GAGTC*ACTGCCACGGAGTGCATCGCGCGGGCC/36-FAM/ |
| F | *GAGTC*ACTGCCACGGAGTGCATCGCGCGGGCC/36-FAM/ |
| G | ATTACA*GAGTC*ACTmGmCCACGGAGTGCATCGCGCGGGCC/36-FAM/ |
| H | /5IAbRQ/GGCCCGCGCGATGCACTCCGTGGCAGTGACTCTGTAAT-C3sp |

A    ATTACA*GAGTC*ACT G CCACGGAGTGCATCGCGCGGCC/36-FAM/

G    ATTACA*GAGTC*ACTmGmCCACGGAGTGCATCGCGCGGCC/36-FAM/

H    /5IAbRQ/GGCCCGCGCGATGCACTCCGTGGCAGTGACTCTGTAAT-C3sp

```
                        SEQUENCE LISTING

<160> NUMBER OF SEQ ID NOS: 46

<210> SEQ ID NO 1
   <211> LENGTH: 38
   <212> TYPE: DNA
   <213> ORGANISM: Artificial Sequence
   <220> FEATURE:
   <223> OTHER INFORMATION: Synthetic oligonucleotide
   <220> FEATURE:
   <223> OTHER INFORMATION: 3'-FAM-Modified

<400> SEQUENCE: 1
attacagagt cactgccacg gagtgcatcg cgcgggcc                           38

<210> SEQ ID NO 2
   <211> LENGTH: 38
   <212> TYPE: DNA
   <213> ORGANISM: Artificial Sequence
   <220> FEATURE:
   <223> OTHER INFORMATION: Synthetic oligonucleotide
   <220> FEATURE:
   <223> OTHER INFORMATION: 5'-Quencher-Modified

<400> SEQUENCE: 2
ggcccgcgcg atgcactccg tggcagtgac tctgtaat                           38

<210> SEQ ID NO 3
   <211> LENGTH: 23
   <212> TYPE: DNA
   <213> ORGANISM: Artificial Sequence
   <220> FEATURE:
   <223> OTHER INFORMATION: Synthetic oligonucleotide
   <220> FEATURE:
   <223> OTHER INFORMATION: 3'-FAM-Modified

<400> SEQUENCE: 3
ccacggagtg catcgcgcgg gcc                                           23

<210> SEQ ID NO 4
   <211> LENGTH: 22
   <212> TYPE: DNA
   <213> ORGANISM: Artificial Sequence
   <220> FEATURE:
   <223> OTHER INFORMATION: Synthetic oligonucleotide

<400> SEQUENCE: 4
```

```
attacagagt cactgccacg ga                                               22

<210> SEQ ID NO 5
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 5
attacagagt cactgccacg gagtgcatcg cgcgggcc                              38

<210> SEQ ID NO 6
<211> LENGTH: 38
<212> TYPE: DNA
<213> ORGANISM: Artificial Sequence
<220> FEATURE:
<223> OTHER INFORMATION: Synthetic oligonucleotide
<220> FEATURE:
<223> OTHER INFORMATION: 5'-5IAbRQ-Modified

<400> SEQUENCE: 6
ggcccgcgcg atgcactccg tggcagtgac tctgtaat                              38

<210> SEQ ID NO 7
<211> LENGTH: 38
<212> TYPE: DNA
<213> ORGANISM: Artificial Sequence
<220> FEATURE:
<223> OTHER INFORMATION: Synthetic oligonucleotide
<220> FEATURE:
<223> OTHER INFORMATION: 3'-36-FAM-Modified

<400> SEQUENCE: 7
attacagagt cactgccacg gagtgcatcg cgcgggcc                              38

<210> SEQ ID NO 8
<211> LENGTH: 38
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (14)..(14)
<223> OTHER INFORMATION: 2'-o-methyl nucleotide
<220> FEATURE:
<223> OTHER INFORMATION: 3'-36-FAM-Modified

<400> SEQUENCE: 8
attacagagt cacugccacg gagtgcatcg cgcgggcc                              38

<210> SEQ ID NO 9
<211> LENGTH: 38
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (16)..(16)
<223> OTHER INFORMATION: 2'-o-methyl nucleotide
<220> FEATURE:
<223> OTHER INFORMATION: 3'-36-FAM-Modified

<400> SEQUENCE: 9
attacagagt cactgccacg gagtgcatcg cgcgggcc                              38
```

<210> SEQ ID NO 10
<211> LENGTH: 38
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (15)..(15)
<223> OTHER INFORMATION: 2'-o-methyl nucleotide
<220> FEATURE:
<223> OTHER INFORMATION: 3'-36-FAM-Modified

<400> SEQUENCE: 10
attacagagt cactgccacg gagtgcatcg cgcgggcc                              38

<210> SEQ ID NO 11
<211> LENGTH: 36
<212> TYPE: DNA
<213> ORGANISM: Artificial Sequence
<220> FEATURE:
<223> OTHER INFORMATION: Synthetic oligonucleotide
<220> FEATURE:
<223> OTHER INFORMATION: 3'-36-FAM-Modified

<400> SEQUENCE: 11
tacagagtca ctgccacgga gtgcatcgcg cgggcc                                36

<210> SEQ ID NO 12
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<223> OTHER INFORMATION: 3'-36-FAM-Modified

<400> SEQUENCE: 12
acagagtcac tgccacggag tgcatcgcgc gggcc                                 35

<210> SEQ ID NO 13
<211> LENGTH: 34
<212> TYPE: DNA
<213> ORGANISM: Artificial Sequence
<220> FEATURE:
<223> OTHER INFORMATION: Synthetic oligonucleotide
<220> FEATURE:
<223> OTHER INFORMATION: 3'-36-FAM-Modified

<400> SEQUENCE: 13
cagagtcact gccacggagt gcatcgcgcg ggcc                                  34

<210> SEQ ID NO 14
<211> LENGTH: 33
<212> TYPE: DNA
<213> ORGANISM: Artificial Sequence
<220> FEATURE:
<223> OTHER INFORMATION: Synthetic oligonucleotide
<220> FEATURE:
<223> OTHER INFORMATION: 3'-36-FAM-Modified

<400> SEQUENCE: 14
agagtcactg ccacggagtg catcgcgcgg gcc                                   33

<210> SEQ ID NO 15
<211> LENGTH: 32
<212> TYPE: DNA
<213> ORGANISM: Artificial Sequence
<220> FEATURE:
<223> OTHER INFORMATION: Synthetic oligonucleotide
<220> FEATURE:
<223> OTHER INFORMATION: 3'-36-FAM-Modified

<400> SEQUENCE: 15
gagtcactgc cacggagtgc atcgcgcggg cc                                    32

<210> SEQ ID NO 16
<211> LENGTH: 38
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (15)..(15)
<223> OTHER INFORMATION: 2'-o-methyl nucleotide
<220> FEATURE:
<221> NAME/KEY: modified_base
<222> LOCATION: (16)..(16)
<223> OTHER INFORMATION: 2'-o-methyl nucleotide
<220> FEATURE:
<223> OTHER INFORMATION: 3'-36-FAM-Modified

<400> SEQUENCE: 16
attacagagt cactgccacg gagtgcatcg cgcgggcc                              38

<210> SEQ ID NO 17
<211> LENGTH: 38
<212> TYPE: DNA
<213> ORGANISM: Artificial Sequence
<220> FEATURE:
<223> OTHER INFORMATION: Synthetic oligonucleotide
<220> FEATURE:
<223> OTHER INFORMATION: 5'-IAbRQ-Modified
<220> FEATURE:
<223> OTHER INFORMATION: 3'-C3 Spacer-Modified

<400> SEQUENCE: 17
ggcccgcgcg atgcactccg tggcagtgac tctgtaat                              38

<210> SEQ ID NO 18
<211> LENGTH: 38
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(7)
<223> OTHER INFORMATION: 2'-o-methyl nucleotide
<220> FEATURE:
<223> OTHER INFORMATION: 3'-36-FAM-Modified

<400> SEQUENCE: 18
attacagagt cactgccacg gagtgcatcg cgcgggcc                              38

<210> SEQ ID NO 19
<211> LENGTH: 38
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (8)..(8)
<223> OTHER INFORMATION: 2'-o-methyl nucleotide
<220> FEATURE:
<223> OTHER INFORMATION: 3'-36-FAM-Modified

<400> SEQUENCE: 19
attacagagt cactgccacg gagtgcatcg cgcgggcc				38

<210> SEQ ID NO 20
<211> LENGTH: 38
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (9)..(9)
<223> OTHER INFORMATION: 2'-o-methyl nucleotide
<220> FEATURE:
<223> OTHER INFORMATION: 3'-36-FAM-Modified

<400> SEQUENCE: 20
attacagagt cactgccacg gagtgcatcg cgcgggcc				38

<210> SEQ ID NO 21
<211> LENGTH: 38
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (10)..(10)
<223> OTHER INFORMATION: 2'-o-methyl nucleotide
<220> FEATURE:
<223> OTHER INFORMATION: 3'-36-FAM-Modified

<400> SEQUENCE: 21
attacagagu cactgccacg gagtgcatcg cgcgggcc				38

<210> SEQ ID NO 22
<211> LENGTH: 38
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (11)..(11)
<223> OTHER INFORMATION: 2'-o-methyl nucleotide
<220> FEATURE:
<223> OTHER INFORMATION: 3'-36-FAM-Modified

<400> SEQUENCE: 22
attacagagt cactgccacg gagtgcatcg cgcgggcc				38

<210> SEQ ID NO 23
<211> LENGTH: 38
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(7)
<223> OTHER INFORMATION: 2'-o-methyl nucleotide
<220> FEATURE:
<221> NAME/KEY: modified_base
<222> LOCATION: (12)..(12)
<223> OTHER INFORMATION: 2'-o-methyl nucleotide
<220> FEATURE:
<223> OTHER INFORMATION: 3'-36-FAM-Modified

<400> SEQUENCE: 23
attacagagt cactgccacg gagtgcatcg cgcgggcc				38

<210> SEQ ID NO 24
<211> LENGTH: 38
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(7)
<223> OTHER INFORMATION: 2'-o-methyl nucleotide
<220> FEATURE:
<221> NAME/KEY: modified_base
<222> LOCATION: (13)..(13)
<223> OTHER INFORMATION: 2'-o-methyl nucleotide
<220> FEATURE:
<223> OTHER INFORMATION: 3'-36-FAM-Modified

<400> SEQUENCE: 24
attacagagt cactgccacg gagtgcatcg cgcgggcc                             38

<210> SEQ ID NO 25
<211> LENGTH: 38
<212> TYPE: DNA
<213> ORGANISM: Artificial Sequence
<220> FEATURE:
<223> OTHER INFORMATION: Synthetic oligonucleotide
<220> FEATURE:
<223> OTHER INFORMATION: 5'-BHQ-1-Modified
<220> FEATURE:
<223> OTHER INFORMATION: 3'-C3 Spacer-Modified

<400> SEQUENCE: 25
ggcccgcgcg atgcactccg tggcagtgac tctgtaat                             38

<210> SEQ ID NO 26
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (6)..(12)
<223> OTHER INFORMATION: n is a, c, g, or t, unknown or other

<400> SEQUENCE: 26
gagtcnnnnn nn                                                         12

<210> SEQ ID NO 27
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(7)
<223> OTHER INFORMATION: n is a, c, g, or t, unknown or other

<400> SEQUENCE: 27
nnnnnnngac tc                                                         12

<210> SEQ ID NO 28
<211> LENGTH: 12
<212> TYPE: DNA
<213> ORGANISM: Artificial Sequence
<220> FEATURE:

<223> OTHER INFORMATION: Description of Artificial Sequence: Synthetic
    oligonucleotide
<220> FEATURE:
<221> NAME/KEY: misc_feature
<222> LOCATION: (5)..(5)
<223> OTHER INFORMATION: n is a, c, g, or t, unknown or other
<220> FEATURE:
<221> NAME/KEY: misc_feature
<222> LOCATION: (7)..(12)
<223> OTHER INFORMATION: n is a, c, g, or t, unknown or other

<400> SEQUENCE: 28
gagtncnnnn nn                                                     12

<210> SEQ ID NO 29
<211> LENGTH: 12
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: misc_feature
<222> LOCATION: (1)..(7)
<223> OTHER INFORMATION: n is a, c, g, or t, unknown or other

<400> SEQUENCE: 29
nnnnnnngac tc                                                     12

<210> SEQ ID NO 30
<211> LENGTH: 10
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: misc_feature
<222> LOCATION: (6)..(10)
<223> OTHER INFORMATION: n is a, c, g, or t, unknown or other

<400> SEQUENCE: 30 ggatcnnnnn                                                        10

<210> SEQ ID NO 31
<211> LENGTH: 10
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: misc_feature
<222> LOCATION: (1)..(5)
<223> OTHER INFORMATION: n is a, c, g, or t, unknown or other

<400> SEQUENCE: 31 nnnnngatcc                                                        10

<210> SEQ ID NO 32
<211> LENGTH: 10
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: misc_feature
<222> LOCATION: (6)..(10)
<223> OTHER INFORMATION: n is a, c, g, or t, unknown or other

```
<400> SEQUENCE: 32 gagtcnnnnn                                                          10

<210> SEQ ID NO 33
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(5)
<223> OTHER INFORMATION: n is a, c, g, or t, unknown or other

<400> SEQUENCE: 33 nnnnngactc                                                          10

<210> SEQ ID NO 34
<211> LENGTH: 10
<212> TYPE: DNA
<213> ORGANISM: Artificial Sequence
<220> FEATURE:
<223> OTHER INFORMATION: enzyme recognition sequence
<220> FEATURE:
<221> NAME/KEY: misc_feature
<222> LOCATION: (6)..(10)
<223> OTHER INFORMATION: n is a, c, g, or t, unknown or other

<400> SEQUENCE: 34 gagtcnnnnn                                                          10

<210> SEQ ID NO 35
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(5)
<223> OTHER INFORMATION: n is a, c, g, or t, unknown or other

<400> SEQUENCE: 35 nnnnngactc                                                          10

<210> SEQ ID NO 36
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (6)..(14)
<223> OTHER INFORMATION: n is a, c, g, or t, unknown or other

<400> SEQUENCE: 36
gagtcnnnnn nnnn                                                     14

<210> SEQ ID NO 37
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: misc_feature
<222> LOCATION: (1)..(9)
<223> OTHER INFORMATION: n is a, c, g, or t, unknown or other

<400> SEQUENCE: 37
nnnnnnnnng actc                                                              14

<210> SEQ ID NO 38
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(4)
<223> OTHER INFORMATION: n is a, c, g, or t, unknown or other
<220> FEATURE:
<221> NAME/KEY: misc_feature
<222> LOCATION: (10)..(15)
<223> OTHER INFORMATION: n is a, c, g, or t, unknown or other
<220> FEATURE:
<221> NAME/KEY: misc_feature
<222> LOCATION: (21)..(24)
<223> OTHER INFORMATION: n is a, c, g, or t, unknown or other

<400> SEQUENCE: 38
nnnngactcn nnnnngagtc nnnn                                                   24

<210> SEQ ID NO 39
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(4)
<223> OTHER INFORMATION: n is a, c, g, or t, unknown or other
<220> FEATURE:
<221> NAME/KEY: misc_feature
<222> LOCATION: (10)..(13)
<223> OTHER INFORMATION: n is a, c, g, or t, unknown or other
<220> FEATURE:
<221> NAME/KEY: misc_feature
<222> LOCATION: (19)..(22)
<223> OTHER INFORMATION: n is a, c, g, or t, unknown or other

<400> SEQUENCE: 39
nnnngactcn nnngagtcnn nn                                                     22

<210> SEQ ID NO 40
<211> LENGTH: 37
<212> TYPE: DNA
<213> ORGANISM: Artificial Sequence
<220> FEATURE:
<223> OTHER INFORMATION: Synthetic primer
<220> FEATURE:
<221> NAME/KEY: modified_base
<222> LOCATION: (25)..(25)
<223> OTHER INFORMATION: 2'-o-methyl nucleotide
<220> FEATURE:
<221> NAME/KEY: modified_base
<222> LOCATION: (33)..(33)
<223> OTHER INFORMATION: 2'-o-methyl nucleotide
<220> FEATURE:
<221> NAME/KEY: modified_base
<222> LOCATION: (34)..(34)
<223> OTHER INFORMATION: 2'-o-methyl nucleotide
<220> FEATURE:
<221> NAME/KEY: modified_base
<222> LOCATION: (35)..(35)
```

```
<223> OTHER INFORMATION: 2'-o-methyl nucleotide
<220> FEATURE:
<221> NAME/KEY: modified_base
<222> LOCATION: (36)..(36)
<223> OTHER INFORMATION: 2'-o-methyl nucleotide
<220> FEATURE:
<221> NAME/KEY: modified_base
<222> LOCATION: (37)..(37)
<223> OTHER INFORMATION: 2'-o-methyl nucleotide

<400> SEQUENCE: 40
tgactccata tggagtcaca tcaccgaaat accgcca                                    37

<210> SEQ ID NO 41
<211> LENGTH: 36
<212> TYPE: DNA
<213> ORGANISM: Artificial Sequence
<220> FEATURE:
<223> OTHER INFORMATION: Synthetic primer
<220> FEATURE:
<221> NAME/KEY: modified_base
<222> LOCATION: (24)..(24)
<223> OTHER INFORMATION: 2'-o-methyl nucleotide
<220> FEATURE:
<221> NAME/KEY: modified_base
<222> LOCATION: (32)..(32)
<223> OTHER INFORMATION: 2'-o-methyl nucleotide
<220> FEATURE:
<221> NAME/KEY: modified_base
<222> LOCATION: (33)..(33)
<223> OTHER INFORMATION: 2'-o-methyl nucleotide
<220> FEATURE:
<221> NAME/KEY: modified_base
<222> LOCATION: (34)..(34)
<223> OTHER INFORMATION: 2'-o-methyl nucleotide
<220> FEATURE:
<221> NAME/KEY: modified_base
<222> LOCATION: (35)..(35)
<223> OTHER INFORMATION: 2'-o-methyl nucleotide
<220> FEATURE:
<221> NAME/KEY: modified_base
<222> LOCATION: (36)..(36)
<223> OTHER INFORMATION: 2'-o-methyl nucleotide

<400> SEQUENCE: 41
gactcgatat cgagtctttc caccgaaata ccgcca                                     36

<210> SEQ ID NO 42
<211> LENGTH: 36
<212> TYPE: DNA
<213> ORGANISM: Artificial Sequence
<220> FEATURE:
<223> OTHER INFORMATION: Synthetic primer
<220> FEATURE:
<221> NAME/KEY: modified_base
<222> LOCATION: (24)..(24)
<223> OTHER INFORMATION: 2'-o-methyl nucleotide
<220> FEATURE:
<221> NAME/KEY: modified_base
<222> LOCATION: (32)..(32)
<223> OTHER INFORMATION: 2'-o-methyl nucleotide
<220> FEATURE:
<221> NAME/KEY: modified_base
<222> LOCATION: (33)..(33)
<223> OTHER INFORMATION: 2'-o-methyl nucleotide
<220> FEATURE:
<221> NAME/KEY: modified_base
<222> LOCATION: (34)..(34)
<223> OTHER INFORMATION: 2'-o-methyl nucleotide
<220> FEATURE:
<221> NAME/KEY: modified_base
<222> LOCATION: (35)..(35)
<223> OTHER INFORMATION: 2'-o-methyl nucleotide
<220> FEATURE:
<221> NAME/KEY: modified_base
```

<222> LOCATION: (36)..(36)
<223> OTHER INFORMATION: 2'-o-methyl nucleotide

<400> SEQUENCE: 42
gaaagactcg cgagtctttc caccgaaata ccgcca                                    36

<210> SEQ ID NO 43
<211> LENGTH: 46
<212> TYPE: DNA
<213> ORGANISM: Artificial Sequence
<220> FEATURE:
<223> OTHER INFORMATION: Synthetic primer
<220> FEATURE:
<221> NAME/KEY: modified_base
<222> LOCATION: (25)..(25)
<223> OTHER INFORMATION: 2'-o-methyl nucleotide
<220> FEATURE:
<221> NAME/KEY: modified_base
<222> LOCATION: (42)..(42)
<223> OTHER INFORMATION: 2'-o-methyl nucleotide
<220> FEATURE:
<221> NAME/KEY: modified_base
<222> LOCATION: (43)..(43)
<223> OTHER INFORMATION: 2'-o-methyl nucleotide
<220> FEATURE:
<221> NAME/KEY: modified_base
<222> LOCATION: (44)..(44)
<223> OTHER INFORMATION: 2'-o-methyl nucleotide
<220> FEATURE:
<221> NAME/KEY: modified_base
<222> LOCATION: (45)..(45)
<223> OTHER INFORMATION: 2'-o-methyl nucleotide
<220> FEATURE:
<221> NAME/KEY: modified_base
<222> LOCATION: (46)..(46)
<223> OTHER INFORMATION: 2'-o-methyl nucleotide

<400> SEQUENCE: 43
tgactccata tggagtcaca tcggcatcat tattatcttt gugaac                         46

<210> SEQ ID NO 44
<211> LENGTH: 45
<212> TYPE: DNA
<213> ORGANISM: Artificial Sequence
<220> FEATURE:
<223> OTHER INFORMATION: Synthetic primer
<220> FEATURE:
<221> NAME/KEY: modified_base
<222> LOCATION: (24)..(24)
<223> OTHER INFORMATION: 2'-o-methyl nucleotide
<220> FEATURE:
<221> NAME/KEY: modified_base
<222> LOCATION: (41)..(41)
<223> OTHER INFORMATION: 2'-o-methyl nucleotide
<220> FEATURE:
<221> NAME/KEY: modified_base
<222> LOCATION: (42)..(42)
<223> OTHER INFORMATION: 2'-o-methyl nucleotide
<220> FEATURE:
<221> NAME/KEY: modified_base
<222> LOCATION: (43)..(43)
<223> OTHER INFORMATION: 2'-o-methyl nucleotide
<220> FEATURE:
<221> NAME/KEY: modified_base
<222> LOCATION: (44)..(44)
<223> OTHER INFORMATION: 2'-o-methyl nucleotide
<220> FEATURE:
<221> NAME/KEY: modified_base
<222> LOCATION: (45)..(45)
<223> OTHER INFORMATION: 2'-o-methyl nucleotide

<400> SEQUENCE: 44
gactcgatat cgagtctttc cggcatcatt attatctttg ugaac                          45

```
<210> SEQ ID NO 45
<211> LENGTH: 45
<212> TYPE: DNA
<213> ORGANISM: Artificial Sequence
<220> FEATURE:
<223> OTHER INFORMATION: Synthetic primer
<220> FEATURE:
<221> NAME/KEY: modified_base
<222> LOCATION: (24)..(24)
<223> OTHER INFORMATION: 2'-o-methyl nucleotide
<220> FEATURE:
<221> NAME/KEY: modified_base
<222> LOCATION: (41)..(41)
<223> OTHER INFORMATION: 2'-o-methyl nucleotide
<220> FEATURE:
<221> NAME/KEY: modified_base
<222> LOCATION: (42)..(42)
<223> OTHER INFORMATION: 2'-o-methyl nucleotide
<220> FEATURE:
<221> NAME/KEY: modified_base
<222> LOCATION: (43)..(43)
<223> OTHER INFORMATION: 2'-o-methyl nucleotide
<220> FEATURE:
<221> NAME/KEY: modified_base
<222> LOCATION: (44)..(44)
<223> OTHER INFORMATION: 2'-o-methyl nucleotide
<220> FEATURE:
<221> NAME/KEY: modified_base
<222> LOCATION: (45)..(45)
<223> OTHER INFORMATION: 2'-o-methyl nucleotide

<400> SEQUENCE: 45
gaaagactcg cgagtctttc cggcatcatt attatctttg ugaac          45

<210> SEQ ID NO 46
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<223> OTHER INFORMATION: 5'-CalRed-Modified
<220> FEATURE:
<223> OTHER INFORMATION: 3'-BHQ2-Modified

<400> SEQUENCE: 46
cgcctgtgaa ctttattggc g          21
```

COMPOSITIONS AND METHODS FOR DETECTING NICKING ENZYME AND POLYMERASE ACTIVITY USING A SUBSTRATE MOLECULE

CROSS-REFERENCE TO RELATED APPLICATION

This application is a Continuation of U.S. Ser. No.: 15/546,582, filed Jul. 26, 2017, now issued U.S. Pat. No. 10,570,441, which is the U.S. National Phase Application, pursuant to 35 U.S.C. § 371, of PCT international application Ser. No.: PCT/US2016/014573, filed Jan. 25, 2016, designating the United States and published in English, which claims priority to U.S. Provisional Application Ser. No. 62/110,237, filed Jan. 30, 2015. The entire content of this application is hereby incorporated by reference herein.

BACKGROUND OF THE INVENTION

Nucleic acid amplification reactions may fail to react because the target nucleic acid is absent (true negative) or because specific amplification is inhibited (false negative). Thus, understanding the source of reaction failure can impact the interpretation of a negative result. The use of a positive control can increase confidence that a negative result is a true negative by ruling out failure due to the reaction components. When nucleic amplification reactions are used as a means of detecting an infectious agent, positive controls are particularly useful for indicating that negative amplifications represent truly negative specimens.

Accordingly, improved methods for accurate detection of target nucleic acid molecules are urgently required.

SUMMARY OF THE INVENTION

The present invention provides compositions and methods for testing the activity of nicking enzyme and polymerase in a reaction involving the use of a nucleic acid substrate molecule that detects nicking enzyme and polymerase extension activities by the release of a detectable reporter (e.g., a fluorophore).

In one aspect, the invention provides a substrate for a nicking and extension reaction including a nucleic acid duplex having a first nucleic acid strand having a nicking enzyme recognition site and a fluorescent detectable label covalently linked at the 3' end; and a second nucleic acid strand having a sequence capable of duplexing with the first strand and a quencher moiety covalently linked at the 5' end or a nucleic acid duplex having a first nucleic acid strand having a nicking enzyme recognition site and a quencher moiety covalently linked at the 3' end; and a second nucleic acid strand having a sequence capable of duplexing with the first strand and a fluorescent detectable label covalently linked at the 5' end.

In another aspect, the invention provides a method of detecting nicking enzyme and polymerase activity in a reaction involving: contacting a nucleic acid duplex with a nicking enzyme, the duplex having: a first nucleic acid strand comprising a nicking enzyme recognition site and a fluorescent detectable label covalently linked at the 3' end; and a second nucleic acid strand having a sequence capable of duplexing with the first strand and a quencher moiety at the 5' end; or the duplex having: a first nucleic acid strand having a nicking enzyme recognition site and a quencher moiety covalently linked at the 3' end; and a second nucleic acid strand having a sequence capable of duplexing with the first strand and a fluorescent detectable label covalently linked at the 5' end; contacting the nicked duplex with a polymerase in the presence of dNTPs; extending the polymerase, thereby displacing the portion of the first nucleic acid strand 3' of the nick site covalently linked to the fluorescent detectable label or quencher moiety; and detecting a signal from the fluorescent detectable label that is separated from the quencher, thereby detecting nicking enzyme and polymerase activity in the reaction.

In still another aspect, the invention provides a method of amplifying a specific product in a nicking amplification reaction involving: contacting a target nucleic acid molecule under substantially isothermal conditions with two or more primers, each of which specifically binds to a target nucleic acid molecule, in the presence of a polymerase, dNTPs, a nicking enzyme, and a duplex having: a first nucleic acid strand having a nicking enzyme recognition site and a fluorescent detectable label covalently linked at the 3' end; and a second nucleic acid strand having a sequence capable of duplexing with the first strand and a quencher moiety at the 5' end; or a duplex having: a first nucleic acid strand having a nicking enzyme recognition site and a quencher moiety covalently linked at the 3' end; and a second nucleic acid strand having a sequence capable of duplexing with the first strand and a fluorescent detectable label covalently linked at the 5' end; generating amplicons containing at least a portion of said target nucleic acid molecule; nicking the duplex and extending the polymerase, thereby displacing the portion of the first nucleic acid strand 3' of the nick site covalently linked to the fluorescent detectable label or quencher moiety; and detecting a signal from the fluorescent detectable label that is separated from the quencher, thereby detecting nicking enzyme and polymerase activity in the reaction.

In another aspect, the invention provides a method of detecting a specific product in a nicking amplification reaction involving: contacting a target nucleic acid molecule under substantially isothermal conditions with two or more primers, each of which specifically binds to a target nucleic acid molecule, in the presence of a polymerase, dNTPs, a nicking enzyme, a detectable polynucleotide probe, and a duplex having: a first nucleic acid strand having a nicking enzyme recognition site and a fluorescent detectable label covalently linked at the 3' end; and a second nucleic acid strand having a sequence capable of duplexing with the first strand and a quencher moiety at the 5' end; or a duplex having: a first nucleic acid strand having a nicking enzyme recognition site and a quencher moiety covalently linked at the 3' end; and a second nucleic acid strand having a sequence capable of duplexing with the first strand and a fluorescent detectable label covalently linked at the 5' end; generating amplicons containing at least a portion of said target nucleic acid molecule; nicking the duplex and extending the polymerase, thereby displacing the portion of the first nucleic acid strand 3' of the nick site covalently linked to the fluorescent detectable label or quencher moiety; detecting a signal from the fluorescent detectable label that is separated from the quencher, thereby detecting nicking enzyme and polymerase activity in the reaction; and detecting a signal specific for oligonucleotide probe hybridization to the target nucleic acid molecule or amplicon thereof, where the signal indicates the quantity of the target nucleic acid molecule present in the sample or an amplicon thereof.

In yet another aspect, the invention provides a kit for detecting nicking enzyme and polymerase activity in a reaction, the kit containing a substrate for a nicking and extension reaction including a nucleic acid duplex having: a first nucleic acid strand having a nicking enzyme recognition site and a fluorescent detectable label covalently linked at the 3' end; and a second nucleic acid strand having a sequence capable of duplexing with the first strand and a quencher moiety at the 5' end; or a nucleic acid duplex having: a first nucleic acid strand having a nicking enzyme recognition site and a quencher moiety covalently linked at the 3' end; and a second nucleic acid strand having a sequence capable of duplexing with the first strand and a fluorescent detectable label covalently linked at the 5' end.

In various embodiments of any aspect delineated herein, the substrate or duplex is between about 30 bp to about 2 kb in length, between about 100 bp to about 1 kb in length, between about 100 to about 500 bp in length, between about 30 to about 200 bp in length, between about 30 to about 60 bp in length, between about 35 to about 50 bp in length. In various embodiments of any aspect delineated herein, the nucleic acid strands of the substrate or duplex are between about 30 to about 2000 nt in length, between about 100 to about 1000 nt in length, between about 100 to about 500 nt in length, between about 30 to about 100 nt in length, between about 30 to about 60 nt in length, between about 35 to about 50 nt in length. In various embodiments of any aspect delineated herein, the length of the nucleic acid strand 3' of the nick site is about 25 nt, about 35 nt, about 40 nt or more. In various embodiments of any aspect delineated herein, the length of the nucleic acid strand 5' of the nick site is 10 nt, about 15 nt, about 20 nt or more. In certain embodiments, the length of the nucleic acid strand 5' of the nicking enzyme recognition site is about 10 nt, about 5 nt, about 3 nt or less. In particular embodiments, the length of the nucleic acid strand 5' of the nicking enzyme recognition site is 4, 3, 2, or 1 nt. In various embodiments of any aspect delineated herein, the first and second nucleic acid strands are covalently linked.

In various embodiments of any aspect delineated herein, the substrate comprises a modified nucleotide. In various embodiments of any aspect delineated herein, the 3' end of the second nucleic acid is modified with a C3 spacer, dideoxy nucleotide, phosphorylation, dye, fluorophore, quencher, spacer, or linker. In various embodiments of any aspect delineated herein, the first nucleic acid strand of the substrate or duplex is modified at one or more nucleotides at position 1, 5' of the nick site (e.g., nick–1), at position 2, 5' of the nick site (e.g., nick –2), and at position 1, 3' of the nick site (e.g., nick+1). In various embodiments of any aspect delineated herein, the first nucleic acid strand of the substrate or duplex is modified at one or more nucleotides (e.g., 1, 2, 3, 4, 5) between the nicking recognition site and the nick site. In various embodiments of any aspect delineated herein, the substrate is modified at one or more positions within the nicking enzyme recognition site.

In various embodiments of any aspect delineated herein, the modified nucleotide is a modified nucleotide comprising a 2'-O-methyl, 2'-methoxyethoxy, 2'-fluoro, 2'-hydroxyl (RNA), 2'-allyl, 2'-O-[2-(methylamino)-2-oxoethyl], 4'-thio, 4'-CH$_2$—O-2'-bridge, 4'-(CH$_2$)$_2$—O-2'-bridge, and 2'-O-(N-methylcarbamate), methylation, biotinylation, nucleotide adduct, or a base analog.

In various embodiments of any aspect delineated herein, the substrate or duplex has a fluorescent detectable label paired with a quencher moiety. In various embodiments of any aspect delineated herein, the fluorescent detectable label is FAM, TET, HEX, TAMRA, JOE, or ROX. In various embodiments of any aspect delineated herein, the quencher moiety is 5' IOWA BLACK® RQ (5IabRQ), dabcyl, dabsyl, or a BLACK HOLE QUENCHER® dye. In various embodiments of any aspect delineated herein, the substrate or duplex contains one or more pairs of a fluorescent detectable label and quencher moiety that are covalently linked (e.g., biotinylated) on opposite nucleic acid strands and internal to the duplex.

In various embodiments of any aspect delineated herein, the reaction is performed under substantially isothermal conditions. In various embodiments of any aspect delineated herein, the reaction further comprises primers, probe, and/or target nucleic acid molecules. In various embodiments of any aspect delineated herein, the nucleic acid strands of the substrate or duplex have sequences that do not bind to other nucleic acid molecules present in the reaction. In various embodiments of any aspect delineated herein, the fluorescent detectable label of the nucleic acid duplex and the fluorescent detectable label of the probe are different (e.g., FAM and CalRed). In various embodiments of any aspect delineated herein, the detection of a signal from the duplex is used as a positive control. In various embodiments of any aspect delineated herein, when the signal from the duplex reaches a set relative fluorescence (RFU) indicates the end point of monitoring the nicking amplification reaction. In various embodiments of any aspect delineated herein, the method involves the use of one or more nucleic acid duplexes or substrate that differ in their modifications.

In various embodiments of any aspect delineated herein, the first nucleic acid strand of the substrate or duplex is nicked by a nicking enzyme. In various embodiments of any aspect delineated herein, the nicking enzyme is Nt.BstNBI, N.Bst9I, N.BstSEI, Nb.BbvCI, Nb.Bpu10I, Nb.BsmI, Nb.BsrDI, Nb.BtsI, Nt.AlwI, Nt.BbvCI, Nt.Bpu10I, Nt.BsmAI, Nt.BspD6I, Nt.BspQI, and Nt.CviPII. In various embodiments of any aspect delineated herein, the first nucleic acid strand of the substrate or duplex is contacted with a polymerase. In various embodiments of any aspect delineated herein, the polymerase is Bst DNA polymerase I, Bsu DNA polymerase, Gst DNA polymerase I, and Gka DNA polymerase I. In other embodiments, exemplary polymerases include, but are not limited to BST (large fragment), DNA polymerase I (*E. coli*), DNA polymerase I, Large (Klenow) fragment, Klenow fragment (3'-5' exo-), T4 DNA polymerase, T7 DNA polymerase, Deep VentR(exo-) DNA Polymerase, Deep VentR DNA Polymerase, DyNAzyme, High-Fidelity DNA Polymerase, Therminator, Therminator II DNA Polymerase, AmpliTherm DNA Polymerase, Taq DNA polymerase, Tth DNA polymerase, Tfl DNA polymerase, Tgo DNA polymerase, SP6 DNA polymerase, Tbr DNA polymerase, or active fragments thereof.

Other features and advantages of the invention will be apparent from the detailed description, and from the claims.

Definitions

By "amplicon" is meant a polynucleotide generated during the amplification of a polynucleotide of interest. In one example, an amplicon is generated during a nicking amplification reaction.

By "amplification rate modifier" is meant an agent capable of affecting the rate of polymerase extension.

By "base substitution" is meant a substituent of a nucleobase polymer that does not cause significant disruption of the hybridization between complementary nucleotide strands.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "complementary" or "complementarity" is meant that a nucleic acid can form hydrogen bond(s) with another nucleic acid sequence by either traditional Watson-Crick or Hoogsteen base pairing. Complementary base pairing includes not only G-C and A-T base pairing, but also includes base pairing involving universal bases, such as inosine. A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, or 10 nucleotides out of a total of 10 nucleotides in the first oligonucleotide being based paired to a second nucleic acid sequence having 10 nucleotides represents 50%, 60%, 70%, 80%, 90%, and 100% complementary respectively). To determine that a percent complementarity is of at least a certain percentage, the percentage of contiguous residues in a nucleic acid molecule that can form hydrogen bonds (e.g., Watson-Crick base pairing) with a second nucleic acid sequence is calculated and rounded to the nearest whole number (e.g., 12, 13, 14, 15, 16, or 17 nucleotides out of a total of 23 nucleotides in the first oligonucleotide being based paired to a second nucleic acid sequence having 23 nucleotides represents 52%, 57%, 61%, 65%, 70%, and 74%, respectively; and has at least 50%, 50%, 60%, 60%, 70%, and 70% complementarity, respectively). As used herein, "substantially complementary" refers to complementarity between the strands such that they are capable of hybridizing under biological conditions. Substantially complementary sequences have 60%, 70%, 80%, 90%, 95%, or even 100% complementarity. Additionally, techniques to determine if two strands are capable of hybridizing under biological conditions by examining their nucleotide sequences are well known in the art.

As used herein, "duplex" refers to a double helical structure formed by the interaction of two single stranded nucleic acids. A duplex is typically formed by the pairwise hydrogen bonding of bases, i.e., "base pairing", between two single stranded nucleic acids which are oriented antiparallel with respect to each other. Base pairing in duplexes generally occurs by Watson-Crick base pairing, e.g., guanine (G) forms a base pair with cytosine (C) in DNA and RNA, adenine (A) forms a base pair with thymine (T) in DNA, and adenine (A) forms a base pair with uracil (U) in RNA. Conditions under which base pairs can form include physiological or biologically relevant conditions (e.g., intracellular: pH 7.2, 140 mM potassium ion; extracellular pH 7.4, 145 mM sodium ion). Furthermore, duplexes are stabilized by stacking interactions between adjacent nucleotides. As used herein, a duplex may be established or maintained by base pairing or by stacking interactions. A duplex is formed by two complementary nucleic acid strands, which may be substantially complementary or fully complementary. Single-stranded nucleic acids that base pair over a number of bases are said to "hybridize."

"Detect" refers to identifying the presence, absence or amount of the analyte to be detected.

By "detectable moiety" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "fragment" is meant a portion of a nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 5, 10, 15, 20, 30, 40, 50, 60, 70, 80, 90, or 100 nucleotides.

By "hybridize" is meant to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507). Hybridization occurs by hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "isolated polynucleotide" is meant a nucleic acid (e.g., a DNA, RNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "melting temperature (Tm)" is meant the temperature of a system in equilibrium where 50% of the molecular population is in one state and 50% of the population is in another state. With regard to the nucleic acids of the invention, Tm is the temperature at which 50% of the population is single-stranded and 50% is double-stranded (e.g., intramolecularly or intermolecularly).

By "monitoring a reaction" is meant detecting the progress of a reaction. In one embodiment, monitoring reaction progression involves detecting nicking activity, polymerase extension, and/or detecting the completion of an amplification reaction.

As used herein, "obtaining" as in "obtaining an agent" includes synthesizing, purchasing, or otherwise acquiring the agent.

As used herein, the term "nucleic acid" refers to deoxyribonucleotides, ribonucleotides, or modified nucleotides, and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, 2' modified nucleotides (e.g., 2'-O-methyl ribonucleotides, 2'-F nucleotides).

As used herein, "modified nucleotide" refers to a nucleotide that has one or more modifications to the nucleoside, the nucleobase, pentose ring, or phosphate group. For example, modified nucleotides exclude ribonucleotides containing adenosine monophosphate, guanosine monophosphate, uridine monophosphate, and cytidine monophosphate and deoxyribonucleotides containing deoxyadenosine monophosphate, deoxyguanosine monophosphate, deoxythymidine monophosphate, and deoxycytidine monophosphate. Modifications include those naturally occurring that result from modification by enzymes that modify nucleotides, such as methyltransferases. Modified nucleotides also include synthetic or non-naturally occurring nucleotides. Synthetic or non-naturally occurring modifications in nucleotides include those with 2' modifications, e.g., 2'-O-methyl, 2'-methoxyethoxy, 2'-fluoro, 2'-hydroxyl (RNA), 2'-allyl, 2'-O-[2-(methylamino)-2-oxoethyl], 4'-thio, 4'-$CH_2$—O-2'-bridge, 4'-$(CH_2)_2$—O-2'-bridge, and 2'-O-(N-methylcarbamate) or those comprising base analogs.

By "nucleotide adduct" is meant a moiety that is bound covalently or otherwise fixed to a standard nucleotide base.

By "nicking agent" is meant a chemical entity capable of recognizing and binding to a specific structure in double stranded nucleic acid molecule and breaking a phosphodiester bond between adjoining nucleotides on a single strand upon binding to its recognized specific structure, thereby creating a free 3'-hydroxyl group on the terminal nucleotide preceding the nick site. In preferred embodiments, the 3' end can be extended by an exonuclease deficient polymerase. Exemplary nicking agents include nicking enzymes, RNAzymes, DNAzymes, and transition metal chelators.

By "palindromic" is meant nucleic acid sequences that are identical or substantially identical when read from 5' to 3' on one strand or 5' to 3' on the complementary strand. A perfect palindrome refers to a sequence having two adjacent subsequences, such that when one subsequence is read from the 5' to 3' direction, it is identical to the other subsequence read from the 3' to 5' direction.

By "polymerase-arresting molecule" is meant a moiety associated with a polynucleotide template/primer that prevents or significantly reduces the progression of a polymerase on the polynucleotide template. Preferably, the moiety is incorporated into the polynucleotide. In one preferred embodiment, the moiety prevents the polymerase from progressing on the template.

By "polymerase extension" is meant the forward progression of a polymerase that matches incoming monomers to their binding partners on a template polynucleotide.

As used herein, "primer-dimer" is meant a dimer of two monomer oligonucleotide primers. In the oligonucleotide primers of the invention, the 5' tail regions of monomer primers dimerize.

By "semi-quantitative" is meant providing an estimate of relative quantity based on an internal control.

By "specific product" is meant a polynucleotide product resulting from the hybridization of primer oligonucleotides to a complementary target sequence and subsequent polymerase mediated extension of the target sequence.

By "substantially isothermal condition" is meant at a single temperature or within a narrow range of temperatures that does not vary significantly. In one embodiment, a reaction carried out under substantially isothermal conditions is carried out at a temperature that varies by only about 1-5° C. (e.g., varying by 1, 2, 3, 4, or 5 degrees). In another embodiment, the reaction is carried out at a single temperature within the operating parameters of the instrument utilized.

By "quantity threshold method" is meant providing an estimate of quantity based on either exceeding or not exceeding in quantity a comparative standard.

By "reference" is meant a standard or control condition. As is apparent to one skilled in the art, an appropriate reference is where an element is changed in order to determine the effect of the element.

By "subject" is meant a mammal, including, but not limited to, a human or non-human mammal, such as a bovine, equine, canine, ovine, or feline.

By "target nucleic acid molecule" is meant a polynucleotide to be analyzed. Such polynucleotide may be a sense or antisense strand of the target sequence. The term "target nucleic acid molecule" also refers to amplicons of the original target sequence.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIGS. 1A-1F depict the structure and mechanism of a nicking and extension reaction substrate. FIG. 1A depicts the structure of the nicking and extension reaction substrate molecule of the invention. FIG. 1B depicts an oligonucleotide duplex having a nick site on one strand that is 5' to a detectable reporter molecule that is attached at the 3' end of the strand (e.g., covalently linked). In the example shown, the detectable reporter is a fluorophore that is in proximity to a quencher, that is at the 5' end of the opposite strand. When the two strands are annealed, the 3' fluorophore (e.g., FAM, HEX) and quencher (e.g., 5IabRQ, BHQ-1) are near each other, and the fluorescent signal is quenched. FIG. 1C shows that the substrate molecule of the invention has a nick enzyme recognition site and is nicked in the presence of a nicking enzyme that binds at the site. FIG. 1D shows that the nicked substrate molecule of the invention has a free 3' end at the nick, which can be contacted by a polymerase. FIG. 1E shows that the extension of the polymerase using the complementary strand as a template. Polymerase extension displaces the portion of the strand 3' of the nick site, which is linked to the detectable reporter. The detectable reporter fluoresces when it is separated from the quencher. FIG. 1F shows that the product of the extension reaction is able to be nicked again. However, the molecule can be designed to prevent or minimize further rounds of nicking and extension.

FIG. 2A is a schematic showing a linear rise in signal from the substrate molecule of the invention in the presence of a nicking enzyme and polymerase as the reaction progresses. A linear rise is expected when the substrate molecule and/or its strands do not interact with any other reaction components. For example, the 3' end of any strand may be blocked by a fluorophore or C3 spacer. FIG. 2B is a schematic showing the use of the substrate molecule of the invention as an exogenous control molecule in a nicking amplification reaction. The substrate molecule can be used as a control to show that a nicking enzyme and polymerase has activity in a nicking amplification reaction. Reaction end points for a nicking amplification reaction can be set as the time at which the exogenous control molecule reaches a set RFU (relative fluorescence unit). For example, this may be used to characterize an amplification signal as positive or negative based on its time of detection.

FIGS. 3A and 3B depict a "longmer" substrate of the invention, which in one example can be used to study polymerase processivity. FIG. 3A depicts the structure of the nicking and "longmer" substrate molecule of the invention. FIG. 3B depicts modifications and factors that can be used to study their effect on polymerase processivity.

FIG. 4 provides sequences used to test the effect of modified nucleotides on the properties of the substrate molecule of the invention. The oligonucleotide strand ExogContBOT that has a 5' quencher 5IabRQ (5' IOWA BLACK® RQ) and was paired with each of the oligonucleotide strands having a 3' fluorophore 36-FAM: vanilla (no modified nucleotides), nick −2 (2'OMe at position 2, 5' of nick site), nick+1 (2'OMe at position 1, 3' of nick site), and nick −1 (2'OMe at position 1, 5' of nick site).

FIG. 5A is a graph depicting the activity of the substrate molecules having the oligonucleotide strands described at FIG. 4 in the presence of 0.3 U/µl nicking enzyme.

FIG. 5B is a graph depicting the activity of the substrate molecules having the oligonucleotide strands described at FIG. 4 in the presence of 0.015 U/µl nicking enzyme.

FIG. 5C is a graph depicting the activity of the substrate molecules having the oligonucleotide strands described at FIG. 4 in the presence of 0.075 U/µl nicking enzyme.

FIG. 5D is a graph depicting the activity of the substrate molecules having the oligonucleotide strands described at FIG. 4 in the presence of 0.00375 U/µl nicking enzyme.

FIG. 5E is a graph depicting the activity of the substrate molecules having the oligonucleotide strands described at FIG. 4 in the presence of 0.0188 U/µl nicking enzyme.

FIG. 6A depicts the reaction curves for a substrate molecule comprising the oligonucleotide strand ExogContBOT that has a 5' quencher 5IabRQ and the vanilla oligonucleotide strand having a 3' fluorophore 36-FAM and no modified nucleotides. FIG. 6B depicts the reaction curves for a substrate molecule comprising the oligonucleotide strand ExogContBOT that has a 5' quencher 5IabRQ and the nick −2 oligonucleotide strand having a 3' fluorophore 36-FAM and a 2'OMe at position 2, 5' of nick site. FIG. 6C depicts the reaction curves for a substrate molecule comprising the oligonucleotide strand ExogContBOT that has a 5' quencher 5IabRQ and the nick −1 oligonucleotide strand having a 3' fluorophore 36-FAM and 2'OMe at position 1, 5' of nick site). FIG. 6D depicts the reaction curves for a substrate molecule comprising the oligonucleotide strand ExogContBOT that has a 5' quencher 5IabRQ and the nick+1 oligonucleotide strand having a 3' fluorophore 36-FAM and 2'OMe at position 1, 3' of nick site.

FIG. 7 depicts the results of a study to determine the effect of the length of the oligonucleotide 5' of the nicking recognition site in the substrate molecule. A graph of the reaction curves is shown for substrate molecules have the specified oligonucleotide pairs. Sequences of the oligonucleotide strands of the substrate molecules are shown below the graph.

FIG. 9A is a graph of the reaction curves for reactions using the substrate molecules having the sequences shown below the graph (A-F). FIG. 9B is a graph of the reaction curves for reactions using the substrate molecules having the sequences shown below the graph (A-F).

DETAILED DESCRIPTION OF THE INVENTION

Figure 2A:
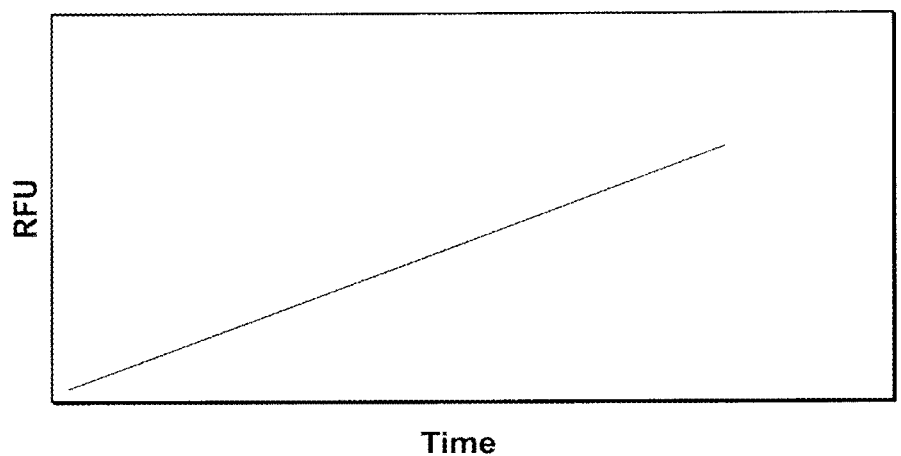
FIGS. 2A and 2B show that nicking and extension of the substrate molecule of the invention results in a linear rise in signal.

The invention features a nucleic acid substrate molecule for nicking and extension reactions having a quenched fluorophore, that is released and able to fluoresce by the activity of a nicking enzyme and polymerase on the substrate. The substrate molecule of the invention can be added to existing nicking amplification reactions, and thus be used as an exogenous control molecule in a nicking amplification reaction. In this regard, the exogenous control molecule provides controls for both the nicking enzyme and polymerase enzyme activities that are present in a nicking amplification reaction. Though running in parallel, the exogenous control reaction does not appreciably interfere with the primary amplification reaction. For example, the exogenous control does not consume large quantities of the reaction components, such as dNTPs. The exogenous control can be designed to minimize the formation of 3' ends, which can lead to non-specific polymerase extension and background interference. As shown herein, the exogenous control molecule can also be 'tuned' to launch at a specific time. On its own, the substrate molecule of the invention can be used in an enzyme performance test or to check enzyme quality.

Nicking and Extension Substrate Molecule

The invention provides a nicking and extension substrate molecule that can be used to test or confirm nicking enzyme and polymerase activities in a reaction. With reference to FIGS. 1A-1E, the substrate molecule comprises an oligonucleotide duplex labeled at one end with a detectable reporter (e.g., fluorophore-quencher pairs; donor-acceptor pair for fluorescence energy transfer (FRET)). In some embodiments, the two oligonucleotide strands are covalently linked. The oligonucleotide duplex contains a nicking enzyme recognition site such that when the molecule is nicked, the 3' end exposed by the nick can drive polymerase extension which results in activation of the detectable reporter. In particular embodiments, the detectable reporter is a fluorescent reporter (e.g., FAM) paired with a quencher molecule (e.g., any interacting fluorophore and quencher pair or FRET donor-acceptor pair known in the art). The fluorescent reporter is activated by the strand displacement activity of the polymerase and separation of the fluorophore from the quencher. The fluorescent reporter is covalently linked to either the 3' or 5' end of the oligonucleotide duplex, and the quencher is covalently linked to the 5' or 3' end, respectively, of the opposite strand. In certain embodiments, the fluorophore is one or more or FAM, TET, HEX, TAMRA, JOE, or ROX. In various embodiments, the quencher is one or more of dabcyl, dabsyl, or a dark quencher dye with an absorbance range across the visible spectrum (BLACK HOLE QUENCHER® dye), including a 5' dark quencher dye with an orange-red absorbance visual spectral range (IOWA BLACK® RQ (5IabRQ) dye). In general, the quenching dye is an excitation matched quenching dye. Fluorophore-quencher pairs and their selection are described for example in Marras, Selection of Fluorophore and Quencher Pairs for Fluorescent Nucleic Acid Hybridization Probes in Methods in Molecular Biology: Fluorescent Energy Transfer Nucleic Acid Probes: Designs and Protocols. Edited by: V. V. Didenko © Humana Press Inc., Totowa, N.J. When the nicking and extension substrate is used as an exogenous control, the detectable fluorescent marker is selected to provide a different detectable fluorescent signal from that used in the probe for detecting target nucleic acid amplification (e.g., FAM and CalRed). In a preferred embodiment, the free 3' end (i.e., not having the fluorescent reporter or quencher) is blocked to prevent its use in polymerase extension reactions. The free 3' may be blocked using a 3 carbon spacer (C3-spacer) or dideoxynucleotide. A number of modifications can be added at the free 3' end during synthesis that prevent extension, including phosphorylation, dye, fluorophore, quencher, spacer, or linker.

The nicking and extension substrate may contain the nicking enzyme recognition site of any nicking enzyme. The nicking enzyme recognition site is positioned such that extension from the 3' end exposed by the nick results in polymerase extension and activation of the detectable reporter. When used as an exogenous control molecule, the nicking enzyme recognition site will be that of the nicking enzyme used in the nicking amplification reaction. Exemplary nicking enzymes include, but are not limited to, N.Bst9I, N.BstSEI, Nb.BbvCI(NEB), Nb.Bpu10I(Fermantas), Nb.BsmI(NEB), Nb.BsrDI(NEB), Nb.BtsI(NEB), Nt.AlwI(NEB), Nt.BbvCI(NEB), Nt.Bpu10I(Fermentas), Nt.BsmAI, Nt.BspD6I, Nt.BspQI(NEB), Nt.BstNBI(NEB), and Nt.CviPII(NEB). Sequences of nicking enzyme recognition sites are provided at Table 1.

TABLE 1

| Nicking enzyme recognition sequences | |
|---|---|
| N.Bst9I | 5'-GAGTCNNNNN↓NN-3'<br>\|\|\|\|\|\|\|\|\| \|\|<br>3'-CTCAGNNNNN•NN-5' |
| N.BstSEI | 5'-GAGTNCNNNN↓NN-3'<br>\|\|\|\|\|\|\|\|\| \|\|<br>3'-CTCAGNNNNN•NN-5' |
| Nb.BbvCI(NEB) | 5'-CCTCA•GC-3'<br>\|\|\|\|\| \|\|<br>3'-GGAGT↑CG-5' |
| Nb.Bpu10I(Fermantas) | 5'-CCTNA•GC-3'<br>\|\|\|\|\| \|\|<br>3'-GGANT↑CG-5' |
| Nb.BsmI(NEB) | 5'-GAATG•CN-3'<br>\|\|\|\|\| \|\|<br>3'-CTTAC↑GN-5' |
| Nb.BsrDI(NEB) | 5'-GCAATG•NN-3'<br>\|\|\|\|\|\| \|\|<br>3'-CGTTAC↑NN-5' |
| Nb.BtsI(NEB) | 5'-GCAGTG•NN-3'<br>\|\|\|\|\|\| \|\|<br>3'-CGTCAC↑NN-5' |
| Nt.AlwI(NEB) | 5'-GGATCNNNN↓N-3'<br>\|\|\|\|\|\|\|\|\| \|<br>3'-CCTAGNNNN•N-5' |
| Nt.BbvCI(NEB) | 5'-CC↓TCAGC-3'<br>\|\| \|\|\|\|\|<br>3'-GG•AGTCG-5' |
| Nt.Bpu10I(Fermentas) | 5'-CC↓TNAGC-3'<br>\|\| \|\|\|\|\|<br>3'-GG•ANTCG-5' |
| Nt.BsmAI | 5'-GTCTCN↓N-3'<br>\|\|\|\|\|\| \|<br>3'-CAGAGN•N-5' |
| Nt.BspD6I | 5'-GAGTCNNNN↓N-3'<br>\|\|\|\|\|\|\|\|\| \|<br>3'-CTCAGNNNN•N-5' |

TABLE 1-continued

Nicking enzyme recognition sequences

```
Nt.BspQI(NEB)       5'-GCTCTTCN↓-3'
                       ||||||||
                    3'-CGAGAAGN  -5'

Nt.BstNBI(NEB)      5'-GAGTCNNNN↓N-3'
                       |||||||||| |
                    3'-CTCAGNNNN•N-5'

Nt.CviPII(NEB)      5'-↓CCD-3'
                       |||
                    3'- GGH-5'
```

In particular embodiments, the nicking enzyme recognition site is Nt.BstNBI for use with the nicking enzyme Nt.BstNBI, which is commonly used in nicking amplification reactions.

The length and nucleic sequence of the nicking and extension substrate molecule may depend on a variety of factors, including its intended use. The length of the substrate molecule is limited only by the length of polynucleotides that can be synthesized by current technologies. However, for some applications like its use as an exogenous reaction control, the length of the substrate may be minimized to make available free dNTPs or other reaction components for nucleic acid amplification. In other applications like its use in studying polymerase processivity, a longer substrate may be used. In various embodiments, the length of the nucleotide duplex is between about 30 bp to about 2 kb in length, between about 100 bp to about 1 kb in length, between about 100 to about 500 bp in length. In other embodiments, the lengths of the polynucleotides of the duplex are between about 30 to about 2000 nt in length, between about 100 to about 1000 nt in length, between about 100 to about 500 nt in length. In various embodiments, the length of the oligonucleotide duplex is between about 30 to about 100 bp in length, between about 30 to about 60 bp in length, between about 35 to about 50 bp in length. In other embodiments, the lengths of the oligonucleotides of the duplex are between about 30 to about 100 nt in length, between about 30 to about 60 nt in length, between about 35 to about 50 nt in length. Likewise, the sequences of the substrate molecule are selected to minimize interference with the sequences of other nucleic acid molecules that may be in the reaction including target nucleic acid sequences, primer sequences, probe sequences, and/or non-specific background sequences (e.g., genomic sequences in a biological sample).

The placement of the nicking enzyme recognition site and/or the nicking enzyme site in the substrate molecule depends on a variety of factors, including the nicking enzyme itself. For example, when the nicking enzyme Nt.BstNBI is used, which generates a nick 3' downstream of its enzyme recognition site, the portion of the oligonucleotide strand 3' of the nick has a duplex melting temperature higher than the highest reaction temperature. The length of the portion of the oligonucleotide strand 3' of the nick is about 25 nt, about 35 nt, about 40 nt or more. Thus, signal generation is coupled to strand displacement by the polymerase.

The length of the portion of the oligonucleotide strand 5' of the nick is about 10 nt, about 15 nt, about 20 nt or more. When the length of the portion of the oligonucleotide strand 5' of the nick has a duplex melting temperature lower than the reaction temperature, polymerase extension off the free 3' end is minimized. For example, the sequence of the region 5' of the nick site can be designed to be unstable at the reaction temperature such that it dissociates, preventing extension from the free 3' end. Alternatively, such shortmers' can be designed to self-bind and 'closeout' a reaction. It has also been found that the substrate molecule has activity when one or more nucleotides are present 5' to the Nt.BstNBI enzyme recognition site. One to about 10 nucleotides, two to about 5 nucleotides, may be present 5' to the Nt.BstNBI enzyme recognition site. Shortening the oligonucleotide strand 5' of the nicking enzyme recognition site changes the reaction rate and provides reaction tunability.

Placement of 2' OMe modified nucleotides in the substrate molecule between the nicking enzyme recognition site and the nick site can alter the reaction rate of the substrate reaction. In some embodiments, the first nucleic acid strand is modified at one or more nucleotides at positions 1 or 2, 5' of the nick site, and position 1, 3' of the nick site. With reference to a duplex comprising a Nt.BstNB1 recognition and nick site, the description of the positions correspond to the numbering (position 1, 2, 3, 4, etc.) and directionality (5' or 3') as shown below:

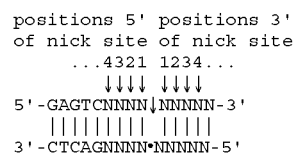

Placement of 2'OMe modified nucleotides in the substrate molecule can be used to 'tune' the reaction (i.e., the reaction rate). One or more of the nucleotides between the nicking enzyme recognition site and the nick site of Nt.BstNBI may be a 2'OMe modified nucleotide. In particular embodiments, the one or more 2'OMe modified nucleotides are positioned at one or more of positions 1 and 2 5' of the nick site and/or at position 1 3' of the nick site.

Reaction tunability may also be achieved using modified nucleotides, branched nucleotides (i.e. T-fam), or any nucleotide which affects the reaction kinetics, including by placing modified nucleotides in the nicking sequence strand; placing modified nucleotides opposite the nicking sequence strand. Reaction tunability may also be achieved by mixing one or more unmodified or modified substrate molecules (e.g., tuning with top/bottom oligo ratios) and/or molarity of nicking enzyme relative to substrate molecule concentration.

Methods of Using the Substrate Molecule

The nicking and enzyme substrate molecule can be used to determine the nicking enzyme and polymerase activity in a reaction. On its own, the substrate molecule can be used to evaluate combinations of nicking enzymes and polymerases, used to identify optimal working conditions of nicking enzymes and polymerases, or check nicking enzyme and polymerase quality. Polymerases for use in the methods described herein are capable of catalyzing the incorporation of nucleotides to extend a 3' hydroxyl terminus of an oligonucleotide (e.g., a primer) bound to a target nucleic acid molecule and/or a 3' hydroxyl terminus at a nick site in a double-stranded DNA molecule in conjunction with strand displacement activity. Exemplary polymerases include, but are not limited to, derivatives and variants of the DNA polymerase I isolated from *Bacillus stearothermophilus*, also classified as *Geobacillus stearothermophilus*, and from closely related bacterial strains, isolates and species comprising the genus *Geobacillus*, which lack or have substantially reduced 5'-3' exonuclease activity and have strand-displacement activity and the large fragments of Bst DNA polymerase I, Bsu DNA polymerase, Gst DNA polymerase I, and Gka DNA polymerase I, and phi29 DNA polymerase. Such polymerases also lack or have substantially reduced 5'-3' exonuclease activity and may include those that are thermophilic (e.g., Taq, Vent). In this regard, the invention also provides a means to quantify the unit activity of combinations of nicking enzymes and polymerases. Additionally, the substrate molecule of the invention may be used to study the processivity of a polymerase under various conditions, including for example, DNA methylation or in the presence of DNA adducts/damage products (e.g., acetaldehyde, cisplatin, 7,12-dimethylbenzanthracene, malondialdehyde, products of base excision repair, oxidative damage products, benzopyrene, aflatoxin, other DNA reactive compounds) and/or DNA binding proteins (FIGS. 3A and 3B). Additionally, for studying processivity one or more fluorophore-quencher pairs, including different, multiple flurophores, may be covalently linked (e.g., biotinylated) internally within the duplex (FIG. 3A). For example, 1-5 fluorophores may be used, one per channel, biotinylated or attached by direct labeling (e.g., succinimidyl esters). One or more overlapping quenchers may be paired on the opposite strand. In some cases, an overlapping quencher covers a broad area of the spectrum and can be paired with multiple, different flurophores. Thus, the substrate molecule of the invention may be modified and the effect of the modifications on polymerase extension and/or processivity be examined.

The substrate molecule of the invention can also be added to existing nicking amplification reactions, and thus be used as an exogenous control molecule in a nicking amplification reaction, for example to verify a true negative reaction. Accordingly, the exogenous control molecule is used at the same reaction temperatures as that for the nicking amplification reaction. The mere presence or absence of signal may be used as a reaction control. Additionally, the time at which the exogenous control reaction reaches a set RFU may signal the end point of a reaction. The exogenous control molecule can also be 'tuned' to a specific reaction rate, thus altering the time to reach a set RFU. When the exogenous control reaction runs in the same reaction as a nicking amplification reaction, it does not appreciably interfere with the primary amplification reaction. The exogenous control does not consume appreciable quantities of the reaction components, such as dNTPs or other reagents. Further, the exogenous control can be designed to minimize the formation of 3' ends, which can lead to non-specific polymerase extension and background interference.

Nucleic Acid Amplification Methods

The polymerase chain reaction (PCR) is a common thermal cycling dependent nucleic acid amplification technology used to amplify DNA consisting of cycles of repeated heating and cooling of the reaction for DNA melting and enzymatic replication of the DNA using a DNA polymerase. Real-Time quantitative PCR (qPCR) is a technique used to quantify the number of copies of a given nucleic acid sequence in a biological sample. Currently, qPCR utilizes the detection of reaction products in real-time throughout the reaction and compares the amplification profile to the amplification of controls which contain a known quantity of nucleic acids at the beginning of each reaction (or a known relative ratio of nucleic acids to the unknown tested nucleic acid). The results of the controls are used to construct standard curves, typically based on the logarithmic portion of the standard reaction amplification curves. These values are used to interpolate the quantity of the unknowns based on where their amplification curves compared to the standard control quantities.

In addition to PCR, non-thermal cycling dependent amplification systems or isothermal nucleic acid amplification technologies exist including, without limitation: Nicking Amplification Reaction, Rolling Circle Amplification (RCA), Helicase-Dependent Amplification (HDA), Loop-Mediated Amplification (LAMP), Strand Displacement Amplification (SDA), Transcription-Mediated Amplification (TMA), Self-Sustained Sequence Replication (3 SR), Nucleic Acid Sequence Based Amplification (NASBA), Single Primer Isothermal Amplification (SPIA), Q-β Replicase System, and Recombinase Polymerase Amplification (RPA).

Isothermal nicking amplification reactions have similarities to PCR thermocycling. Like PCR, nicking amplification reactions employ oligonucleotide sequences which are complementary to a target sequences referred to as primers. In addition, nicking amplification reactions of target sequences results in a logarithmic increase in the target sequence, just as it does in standard PCR. Unlike standard PCR, the nicking amplification reactions progress isothermally. In standard PCR, the temperature is increased to allow the two strands of DNA to separate. In nicking amplification reactions, the target nucleic acid sequence is nicked at specific nicking sites present in a test sample. The polymerase infiltrates the nick site and begins complementary strand synthesis of the nicked target nucleotide sequence (the added exogenous DNA) along with displacement of the existing complimentary DNA strand. The strand displacement replication process obviates the need for increased temperature. At this point, primer molecules anneal to the displaced complementary sequence from the added exogenous DNA. The polymerase now extends from the 3' end of the template, creating a complementary strand to the previously displaced strand. The second oligonucleotide primer then anneals to the newly synthesized complementary strand and extends making a duplex of DNA which includes the nicking enzyme recognition sequence. This strand is then liable to be nicked with subsequent strand displacement extension by the polymerase, which leads to the production of a duplex of DNA which has nick sites on either side of the original target DNA. Once this is synthesized, the molecule continues to be amplified exponentially through replication of the displaced strands with new template molecules. In addition, amplification also proceeds linearly from each product molecule through the repeated action of the nick translation synthesis at the template introduced nick sites. The result is a very rapid increase in target signal amplification; much more rapid than PCR thermocycling, with amplification results in less than ten minutes.

Nicking Amplification Assays

The invention provides a substrate molecule for use with the detection of target nucleic acid molecules amplified in an isothermal nicking amplification assay. Such assays are known in the art and described herein. See, for example, US Patent Application Publication 2009/0081670, PCT Application 2009/012246, and U.S. Pat. Nos. 7,112,423 and 7,282,328, each of which is incorporated herein in its entirety.

Polymerases useful in the methods described herein are capable of catalyzing the incorporation of nucleotides to extend a 3' hydroxyl terminus of an oligonucleotide (e.g., a primer) bound to a target nucleic acid molecule and/or a 3' hydroxyl terminus at a nick site in a double-stranded DNA molecule in conjunction with strand displacement activity. Such polymerases also lack or have substantially reduced 5'-3' exonuclease activity and may include those that are thermophilic. DNA polymerases useful in methods involving primers having 2'-modified nucleotides in the primer region comprising the six 3'-terminal nucleotides include derivatives and variants of the DNA polymerase I isolated from *Bacillus stearothermophilus*, also classified as *Geobacillus stearothermophilus*, and from closely related bacterial strains, isolates and species comprising the genus *Geobacillus*, which lack or have substantially reduced 5'-3' exonuclease activity and have strand-displacement activity. Exemplary polymerases include, but are not limited to, the large fragments of Bst DNA polymerase I, Bsu DNA polymerase, phi29 DNA polymerase, Gst DNA polymerase I, and Gka DNA polymerase I. In other embodiments, exemplary polymerases include, but are not limited to BST (large fragment), DNA polymerase I (*E. coli*), DNA polymerase I, Large (Klenow) fragment, Klenow fragment (3'-5' exo-), T4 DNA polymerase, T7 DNA polymerase, Deep VentR(exo-) DNA Polymerase, Deep VentR DNA Polymerase, DyNAzyme, High-Fidelity DNA Polymerase, Therminator, Therminator II DNA Polymerase, AmpliTherm DNA Polymerase, Taq DNA polymerase, Tth DNA polymerase, Tfl DNA polymerase, Tgo DNA polymerase, SP6 DNA polymerase, Tbr DNA polymerase.

A nicking agent useful in methods described herein is a chemical entity capable of recognizing and binding to a specific structure in double stranded nucleic acid molecules and breaking a phosphodiester bond between adjoining nucleotides on the top strand with a substantially higher rate than breaking the phosphodiester bond between adjoining nucleotides on the bottom strand upon binding to its recognized specific structure, thereby creating a free 3'-hydroxyl group on the terminal nucleotide preceding the nick site that can be extended by a 5'-3'-exonuclease deficient strand displacement polymerase. In a preferred embodiment of the methods disclosed herein, the top strand phosphodiester bond cleavage rate of the "nicking agent" approaches 100%, while the cleavage rate of the bottom strand phosphodiester bond approaches 0%. Nicking agents useful in methods described herein, can either be enzymes, i.e self-regenerating catalysts turning over multiple substrate molecules, or non-regenerating catalysts turning over just a single substrate molecule at an equimolar ratio fashion.

A nicking enzyme binds double-stranded DNA and cleaves one strand of a double-stranded duplex. In the methods of the invention, the nicking enzyme cleaves the top stand (the strand comprising the 5'-3' sequence of the nicking agent recognition site). In a particular embodiment of the invention disclosed herein, the nicking enzyme cleaves the top strand only and 3' downstream of the recognition site. In exemplary embodiments, the reaction comprises the use of a nicking enzyme that cleaves or nicks downstream of the binding site such that the product sequence does not contain the nicking site. Using an enzyme that cleaves downstream of the binding site allows the polymerase to more easily extend without having to displace the nicking enzyme. Ideally, the nicking enzyme is functional under the same reaction conditions as the polymerase. Exemplary nicking enzymes include, but are not limited to, N.Bst9I, N.BstSEI, Nb.BbvCI(NEB), Nb.Bpu10I(Fermantas), Nb.BsmI(NEB), Nb.BsrDI(NEB), Nb.BtsI(NEB), Nt.AlwI(NEB), Nt.BbvCI(NEB), Nt.Bpu10I(Fermentas), Nt.BsmAI, Nt.BspD6I, Nt.BspQI(NEB), Nt.BstNBI(NEB), and Nt.CviPII(NEB). Sequences of nicking enzyme recognition sites are provided at Table 1.

Nicking enzymes also include engineered nicking enzymes created by modifying the cleavage activity of restriction endonucleases (NEB expressions July 2006, vol 1.2). when restriction endonucleases bind to their recognition sequences in DNA, two catalytic sites within each enzyme for hydrolyzing each strand drive two independent hydrolytic reactions which proceed in parallel. Altered restriction enzymes can be engineered that hydrolyze only one strand of the duplex, to produce DNA molecules that are "nicked" (3"-hydroxyl, 5'-phosphate), rather than cleaved. Nicking enzymes may also include modified CRISPR/Cas proteins, Transcription activator-like effector nucleases (TALENs), and Zinc-finger nucleases having nickase activity.

A nicking amplification reaction typically comprises nucleotides, such as, for example, dideoxyribonucleoside triphosphates (dNTPs). The reaction may also be carried out in the presence of dNTPs that comprise a detectable moiety including but not limited to a radiolabel (e.g., $^{32}P$, $^{33}P$, $^{125}I$, $^{35}S$) an enzyme (e.g., alkaline phosphatase), a fluorescent label (e.g., fluorescein isothiocyanate (FITC)), biotin, avidin, digoxigenin, antigens, haptens, or fluorochromes. The reaction further comprises certain salts and buffers that provide for the activity of the nicking enzyme and polymerase.

Advantageously, the nicking amplification reaction is carried out under substantially isothermal conditions where the temperature of the reaction is more or less constant during the course of the amplification reaction. Because the temperature does not need to be cycled between an upper temperature and a lower temperature, the nicking amplification reaction can be carried out under conditions where it would be difficult to carry out conventional PCR. Typically, the reaction is carried out at about between 35 C and 90 C (e.g., about 35, 37, 42, 55, 60, 65, 70, 75, 80, or 85° C.). Advantageously, it is not essential that the temperature be maintained with a great degree of precision. Some variability in temperature is acceptable.

Sets of primers for amplification reactions are selected as having AAG's≤–15, –16, 17, –18, –19, –20, –25, –30 kcal/mole or more. The performance characteristics of amplification reactions may be altered by increasing the concentration of one or more oligonucleotides (e.g., one or more primers and/or probes) and/or their ratios. High concentrations of primers also favor primer-dimer formation. In various embodiments, concentration of a primers is 100, 200, 300, 400, 500, 600, 700, 800, 900, 1000 nM or more. Melt temperature (Tm) and reaction rate modifiers may also be used to lower the melting temperature of the oligonucleotides, such as (but not limited to) ethylene glycol and glycerol. In addition, DNA polymerase reaction rate modifiers (such as dNTP and magnesium concentration) may be used to alter the reaction rate to lead to a greater quantification precision. In particular embodiments, the 5' tail sequences of the forward and reverse primers have the same nucleic acid sequence.

This invention provides methods of monitoring a nicking amplification reaction in real time. In one embodiment, quantitative nucleic acid amplification utilizes target nucleic acids amplification alongside a control amplification of known quantity. The amount of target nucleic acid can be calculated as an absolute quantification or a relative quantification (semi-quantitative) based on the source of the control (exogenous or endogenous control).

Quantification of the unknown nucleotide sequence can be achieved either through comparison of logarithmic threshold amplification of the unknown to a series of known target sequences in either a separate set of reactions or in the same reaction; or as an internal endogenous or exogenous co-amplification product which produces a threshold value, indicative of either a positive result (if the unknown exceeds the threshold) or negative result (if the unknown does not exceed the threshold).

The invention also provides a method of designing a nicking agent-dependent isothermal strand-displacement amplification assay without experimental screening of a multitude of combinations of candidate forward primers and/or candidate reverse primers. A 35 to 70 bp long region within the target sequence is identified having a 12 to 20 bp sequence in the central portion with a Tm≥the assay temperature (e.g., ~55° C.). Adjacent sequences 12 bp to 20 bp long immediately downstream and upstream of the 15 to 20 bp long central region are identified, according to the above criteria. The Tm of the chosen double stranded downstream and upstream adjacent sequences deviate from each other by less than ±3° C. A target-specific pair of forward and reverse primers are created by attaching a 5'-tail region for a stable dimer-forming primer to the 5'-terminus of the 12-20 base upstream adjacent sequence and to the 5'-terminus of the complementary strand of the 12-20 base downstream adjacent sequence. When combining the forward primer, reverse primer, and a probe, the primer driving the synthesis of the strand complementary to the probe is in excess over the other primer at a molar ratio of about 1.1:1 to 10:1. The combined concentration of a primer in the assay is no higher than 1000 nM. The assay design method can also be used to convert a pre-validated PCR assay for an amplicon ≤70 bp to a nicking agent-dependent isothermal strand-displacement amplification assay.

Primer Design

Conventional methods for primer design have focused on primer melting temperature, primer annealing temperature, GC (guaninine and cytosine) content, primer length, and minimizing interactions of the primer with all but the target nucleic acid (see e.g., www.premierbiosoft.com/tech_notes/PCR_Primer_Design.html). Contrary to these methods, it has been found that primers that form stable primer/dimers, expressed in terms of free energy of formation ($\Delta G$), function predictably in nucleic acid amplification reactions. While Free Energy ($\Delta G$) and Melting Temperature (Tm) share primary components Enthalpy ($\Delta H$) and Entropy ($\Delta S$), $\Delta G$ and Tm values are derived differently and have no correlative relationship, and the only way to relate a given $\Delta G$ with a given Tm value is to explicitly know the value of $\Delta H$ and $\Delta S$ from which they are derived (Manthey, "mFold, Delta G, and Melting Temperature" ©2005 and 2011 Integrated DNA Technologies). FIGS. 1-11 relate to the design of optimal primers.

The free energy of formation ($\Delta G$) for intermolecular primer structures may be calculated using formulas known in the art. A number of programs are available for determining the formation of various intramolecular and intermolecular primer structures and calculating their $\Delta G$'s, including for example mfold and UNAfold prediction algorithms (see e.g., Markham and Zuker. UNAFold: Software for Nucleic Acid Folding and Hybridization. Bioinformatics: Volume 2, Chapter 1, pp 3-31, Humana Press Inc., 2008; Zuker et al. Algorithms and Thermodynamics for RNA Secondary Structure Prediction: A Practical Guide In RNA Biochemistry and Biotechnology, 11-43, NATO ASI Series, Kluwer Academic Publishers, 1999; M. Zuker. Prediction of RNA Secondary Structure by Energy Minimization. Methods in Molecular Biology, 267-294, 1994; Jaeger et al. Predicting Optimal and Suboptimal Secondary Structure for RNA. In Molecular Evolution: Computer Analysis of Protein and Nucleic Acid Sequences, Methods in Enzymology 183, 281-306, 1990; Zuker. On Finding All Suboptimal Foldings of an RNA Molecule. Science 244, 48-52, 1989). OligoAnalyzer 3.1 is one such implementation of mfold for primer design (www.idtdna.com/analyzer/Applications/OligoAnalyzer/). For example, with reference to OligoAnalyzer 3.1, $\Delta G$ calculations may be performed using the following parameters: Target Type: DNA; Oligo Concentration 0.25 µM; $Na^+$ Concentration: 60 mM; $Mg^{++}$ Concentration: 15 mM; and dNTPs Concentration: 0.3 mM.

3' Recognition Region

The invention provides a primer having a 3' recognition sequence whose primer-target formation is stable ($\Delta G \leq$ about −20 kcal/mol or more) and has the potential to enhance nucleic acid amplification reaction performance. The 3' recognition region specifically binds to a nucleic acid molecule, for example a complementary sequence of the nucleic acid molecule. In certain embodiments, the 3' recognition region has a sequence that is complementary to 12, 13, 14, 15, 16, 17, 18, 19, or 20 bases or more of a nucleic acid sequence. In particular embodiments, the 3' recognition region comprises one or more inosine bases. In specific embodiments, the 3' recognition region comprises no more than 2/12 inosines. In various embodiments, the primer-target melting temperature is equal to or greater than 8° or 6° C. below the reaction or extension temperature of the assay (Tm≥assay temperature−8°). In particular embodiments, the 3' recognition sequence comprises 12-20, 12-17, or 12-14 bases. In particular embodiments, the primer-target formation is more stable than self dimer formation (e.g., $\Delta\Delta G \leq$ about −15, −16, −17, −18, −19, −20 kcal/mol or more). Preferably, the 3' recognition sequence does not contain self-complementary sequences, short inverted repeats (e.g., >4 bases/repeat), or sequences that otherwise promote intramolecular interactions, which have the potential to interfere with primer-target annealing.

In one embodiment, a primer is designed having a Tm of 56° C. with 4 sequence specific bases at the end of the primer that may not contribute to annealing. In one embodiment, the primer is a 16, 17, 18, 19, 20 or 21-mer.

In particular, a primer of the invention having a 3' recognition sequence is useful in nicking amplification assays. Additionally, the target specific 3' recognition region comprises one or more 2' modified nucleotides (e.g., 2'-O-methyl, 2'-methoxyethoxy, 2'-fluoro, 2'-alkyl, 2'-allyl, 2'-O-[2-(methylamino)-2-oxoethyl], 2'-hydroxyl (RNA), 4'-thio, 4'-$CH_2$—O-2'-bridge, 4'-$(CH_2)_2$—O-2'-bridge, and 2'-O-(N-methylcarbamate)). Without being bound to theory, it is hypothesized that incorporating one or more 2' modified nucleotides in the recognition regions reduces or eliminates intermolecular and/or intramolecular interactions of primers/templates (e.g., primer-dimer formation), and, thereby, reduces or eliminates the background signal in isothermal amplification. The 2' modified nucleotide preferably has a base that base pairs with the target sequence. In particular embodiments, two or more 2' modified nucleotides (e.g., 2, 3, 4, 5 or more 2' modified nucleotides) in the target specific recognition region are contiguous (e.g., a block of modified nucleotides). In some embodiments, the block of 2' modified nucleotides is positioned at the 3' end of the target specific recognition region. In other embodiments, the block of 2' modified nucleotides is positioned at the 5' end of the target specific recognition region. When the block of 2' modified nucleotides is positioned at the 5' end of the target specific recognition region, the 2' modified nucleotides may be separated from the nick site by one or more non-modified nucleotides (e.g., 2, 3, 4, 5 or more 2' unmodified nucleotides). Applicants have found that positioning of one or more 2' modified nucleotides or of a block of 2' modified nucleotides alters the kinetics of amplification. When the one or more 2' modified nucleotides or block of 2' modified nucleotides are positioned at or near the 5' end of the recognition region or proximal to the nick site, real-time amplification reactions showed decreased time to detection. Additionally, the signal curve is contracted and the slope of the curve shifted.

In a related embodiment, ratios of a primer having one or more 2' modified nucleotides can be used to alter the time-to-detection and/or the efficiency of the reaction for the 'tuning' of reactions, resulting in a predictable control over reaction kinetics. Increasing the ratio of primer having one or more 2' modified nucleotides at the 3' end of the recognition sequence to primer having one or more 2' modified nucleotides at the 5' end of the recognition sequence contracted the signal curve and shifted the slope of the curve. It is advantageous to be able to "tune" a reaction providing a means to manipulate both the time-to-detection as well as the efficiency of the reaction. Relative quantification using an internal control requires that two important conditions be met. First, it is beneficial to be able to modify a reaction's time-to-detection creating a non-competitive reaction condition. Thus, by affecting the control reaction to be detectable at a later time-point (relative to the target of interest) the control reaction does not out-compete the specific target of interest even when the target of interest is in low initial abundance. Second, to ensure a true relative abundance calculation, it is required that the control and specific target reactions have matched efficiencies. By controlling the efficiency of each reaction using a "tuning" condition enables reactions to be matched allowing for satisfactory relative quantification calculations. Tuning the reactions can be used to match efficiencies of target nucleic acid amplification and reference nucleic amplification (e.g., internal standard) in quantitative PCR (qPCR). Additionally, amplification curves of the target nucleic acid and the internal standard may be altered so time of detection of their amplification products are separated, while providing the same efficiency for target nucleic acid amplification and internal standard amplification. Through the use of specific combinations and ratios of oligonucleotide structures within a reaction it is possible to create conditions which enable tuned reaction performance.

5' Tail Dimerization Region

The invention provides a primer having a 5' tail region capable of self-dimerization that enhances nucleic acid amplification reaction performance. Without being bound to theory, in a nucleic acid amplification reaction the primer anneals to the target nucleic acid as a primer-dimer. For example, nicking amplification primers have a nicking agent recognition site present at the 5' end that is unrelated to the binding specificity of the primer for the target recognition sequence. Non-specific background products from non-specific primer interactions have the potential to sequester reaction components that would otherwise have been utilized for the amplification of the specific product. In various embodiments, homodimer formation is stable (e.g., $\Delta G \leq$ about $-30, -35, -40, -45, -50, -55, -60$ kcal/mol or more). In various embodiments, the homodimer has a melting temperature higher than the extension reaction temperature. In particular embodiments, the 5' tail region has a sequence that is a palindrome. In further embodiments, the 5' tail region is at least 20 bases (e.g., 20, 21, 22, 23, 24 bases) in length. In additional embodiments, the 5' tail region has a GC content of 80-90%. In certain embodiments, homodimer formation is more stable than formation of other less stable primer dimer conformations formation (e.g., $\Delta\Delta G \leq$ about $-12, -13, -14, -15, -16, -17, -18, -19, -20, -25, -30, -35, -40$ kcal/mol or more).

In particular, a primer of the invention having a 5' tail sequence is useful in nicking amplification reactions. For use in nicking amplification reactions, the 5' tail region comprises one or more nicking agent recognition sites and the 5' tail region has a symmetrically inverted sequence. In particular embodiments, the 5' tail region contains an even number of nucleotides (e.g., 22, 24 nucleotides). The nick site is designed to be positioned between the nucleotide at the 3' end of the 5' tail region and the nucleotide at the 5' end of the 3' recognition region. Without being bound to theory, the nicking enzyme does not cleave at the nick site when the 3' recognition is single-stranded. However, cleavage at the nick site occurs when the 3' recognition region is double stranded (e.g., when the primer is incorporated into a double-stranded target nucleic acid molecule during the course of the nucleic acid amplification reaction). Exemplary 5' tail region sequences 24 nucleotides in length having a Nt.BstNBI recognition sequence can be generated based on the following template 5'-NNNNGACTCNNNNNN-GAGTCNNNN-3'. Based on this template, there are 537,824 5' tail sequences having the following properties: $\Delta G=-48$ Kcal/mole to $-62$ kcal/mole; $\Delta\Delta G<-40$ kcal/mole; and GC content 68% to 84%. Of these, 1050 selected sequences are provided, representing 0.2% of the entire sequence space (248,832). Exemplary 5' tail region sequences 22 nucleotides in length having a Nt.BstNBI recognition sequence and based on the following template 5'-NNNNGACTCNNNN-GAGTCNNNN-3'. Based on this template, there are 248,832 5' tail sequences having the following properties: $\Delta G=-47$ Kcal/mole to $-55$ kcal/mole; $\Delta\Delta G<-40$ kcal/mole; and GC content 72% to 82%. Of these, 200 selected sequences are provided, representing 0.08% of the entire sequence space (248,832).

Target Nucleic Acid Molecules

Methods and compositions of the invention are useful for the amplification and/or identification of a nucleic acid molecule in a test sample. The target sequences are amplified from virtually any samples that comprises a nucleic acid molecule.

Exemplary test samples include body fluids (e.g. saliva, sweat, tears, fluids accumulating in a bodily cavity, urine, ejaculate, vaginal secretion, cerebrospinal fluid, lymph, feces, sputum, decomposition fluid, vomit, sweat, breast milk, blood, serum, and plasma), tissue extracts, culture media (e.g., a liquid in which a cell, such as a pathogen cell, has been grown), environmental samples, agricultural products or other foodstuffs, and their extracts, and DNA identification tags. If desired, the sample is purified prior to inclusion in a nicking amplification reaction using any standard method typically used for isolating a nucleic acid molecule from a biological sample.

In one embodiment, primers amplify a target nucleic acid of a pathogen to detect the presence of the pathogen in a sample. For environmental applications, test samples may include water, liquid extracts of building materials (e.g., drywall, ceiling tiles, wall board, fabrics, wall paper, and floor coverings) that may have been exposed to a subject infected with a pathogen, environmental swabs, or any other sample.

Applications

Target nucleic acid amplification using primers of the invention have characteristics useful for rapid detection of target nucleic acid molecules. Compositions and methods of the invention are useful in human diagnostics, where a rapid diagnostic answer is desired (e.g., detectable amplification in under 20, 15, 10, 9, 8, 7, 6, 5 minutes or less). In particular embodiments, the invention provides for the use of a nicking amplification reaction assay in human or veterinary diagnostics in clinical settings or in the field. In other embodiments, the invention provides for the use of nicking amplification reaction assays in diagnostic field work, where access to thermocycling equipment is unavailable or would be prohibitively expensive. In still other embodiments, the invention provides for the use of nicking amplification reaction assays in a clinical setting where rapid quantitative answers are desired.

Detectable Oligonucleotide Probes

The present invention provides for the quantitative detection of target nucleic acid molecules or amplicons thereof in a nicking amplification reaction using non-amplifiable detectable polynucleotide probes comprising at least one polymerase-arresting molecule (e.g., nucleotide modification or other moiety that renders the oligonucleotide capable of binding a target nucleic acid molecule, but incapable of supporting template extension utilizing the detectable oligonucleotide probe as a target). Without wishing to be bound by theory, the presence of one or more moieties which does not allow polymerase progression likely causes polymerase arrest in non-nucleic acid backbone additions to the oligonucleotide or through stalling of a replicative polymerase (i.e. C3-spacer, damaged DNA bases, other spacer moiety, 2'-OMe bases). These constructs thus prevent or reduce illegitimate amplification of the probe during the course of a nicking amplification reaction. This distinguishes them from conventional detection probes, which must be added at the end of the nicking amplification reaction to prevent their amplification.

Conventional detection probes have proven impractical for quantitating a nicking amplification reaction in real time. If conventional detection probes are incorporated into the nicking amplification reaction, these conventional detection probes are amplified concurrently with the target. The amplification of these detection molecules masks the detection of legitimate target amplicons due to the number of starting molecules of the detection probe at the start of the reaction.

The invention provides non-amplifiable detectable polynucleotide probe that comprise least one polymerase-arresting molecule. A polymerase-arresting molecule of the invention includes, but is not limited to, a nucleotide modification or other moiety that blocks template extension by replicative DNA polymerases, thereby preventing the amplification of detection molecules; but can allow proper hybridization or nucleotide spacing to the target molecule or amplified copies of the target molecule. In one embodiment, a detectable oligonucleotide probe of the invention comprises a 3 carbon spacer (C3-spacer) that prevents or reduces the illegitimate amplification of a detection molecule.

In one embodiment, a detectable oligonucleotide probe comprises one or more modified nucleotide bases having enhanced binding affinity to a complementary nucleotide. Examples of modified bases include, but are not limited to 2' Fluoro amidites, and 2'OMe RNA amidites (also functioning as a polymerase arresting molecule). Detectable oligonucleotide probes of the invention can be synthesized with different colored fluorophores and may be designed to hybridize with virtually any target sequence. In view of their remarkable specificity, a non-amplifiable detectable polynucleotide probe of the invention is used to detect a single target nucleic acid molecule in a sample, or is used in combination with detectable oligonucleotide probes each of which binds a different target nucleic acid molecule. Accordingly, the non-amplifiable detectable polynucleotide probes of the invention may be used to detect one or more target nucleic acid molecules in the same reaction, allowing these targets to be quantitated simultaneously. The present invention encompasses the use of such fluorophores in conjunction with the detectable oligonucleotide probes described herein.

Implementation in Hardware and/or Software

The methods described herein can be implemented on general-purpose or specially programmed hardware or software. For example, the methods can be implemented by a computer readable medium. Accordingly, the present invention also provides a software and/or a computer program product configured to perform the algorithms and/or methods according to any embodiment of the present invention. It is well-known to a skilled person in the art how to configure software which can perform the algorithms and/or methods provided in the present invention. The computer-readable medium can be non-transitory and/or tangible. For example, the computer readable medium can be volatile memory (e.g., random access memory and the like) or non-volatile memory (e.g., read-only memory, hard disks, floppy discs, magnetic tape, optical discs, paper table, punch cards, and the like). The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., $2^{nd}$ ed., 2001).

The present invention may also make use of various computer program products and software for a variety of purposes, such as probe design, management of data, analysis, and instrument operation. (See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.) Additionally, the present invention may have preferred embodiments that include methods for providing genetic information over networks such as the Internet as shown in U.S. Ser. Nos. 10/197,621, 10/063,559 (US Pub No 20020183936), Ser. Nos. 10/065,856, 10/065,868, 10/328,818, 10/328,872, 10/423,403, and 60/482,389.

Kits

The invention provides kits for assaying nicking enzyme and polymerase activity. In various embodiments, the kits include the substrate molecule of the invention. The invention also provides kits for the amplification of a nucleic acid molecule, including the substrate molecule of the invention for use as an exogenous control. Such kits are useful for the detection or quantitation of a nucleic acid in a biological sample obtained from a subject. Kits of the present invention may comprise, for example, DNA polymerases, forward and reverse primers, and one or more nicking enzymes, as described herein, and a detectable probe. Where multiple pathogen sequences are to be amplified, and the templates designed for those target sequences comprise the nicking enzyme sites for the same nicking enzyme, then one or two nicking enzymes may be included. Where the templates are recognized by different nicking enzymes, more nicking enzymes may be included in the kit, such as, for example, 3 or more.

In one aspect, the invention provides a kit for nucleic acid amplification comprising a DNA polymerase; a primary primer, a secondary primer, a nicking enzyme with specificity to a nicking enzyme binding site within the primers, and deoxynucleotide triphosphates (dNTP's) (e.g., in a buffered solution containing components sufficient for amplification. In various embodiments, the primary primer and secondary primer, each have a 3'-end specific recognition region sequence complementary or substantially complementary to the target sequence, where the end specific recognition region comprises one or more 2' modified nucleotides; a 5'-end tail region containing a nicking enzyme binding site upstream of the 3'-end specific recognition region sequences that is able to dimerize with itself (e.g., self-complementary). In particular embodiments, one or more primers are in a primer-dimer configuration (e.g., produced by heating about Tm and slow cooling).

The kits of the present invention may also comprise one or more of the components in any number of separate containers, packets, tubes (e.g., <0.2 ml, 0.2 ml, 0.6 ml, 1.5 ml, 5.0 ml, >5.0 ml), vials, microtiter plates (e.g., <96-well, 96-well, 384-well, 1536-well, >1536-well), ArrayTape, and the like, or the components may be combined in various combinations in such containers. In various embodiments, the kit further comprises a pair of primers capable of binding to and amplifying a reference sequence. In particular embodiments, the kit comprises one or more primers in a primer-dimer configuration (e.g., produced by heating about Tm and slow cooling). In yet other embodiments, the kit comprises a sterile container which contains the primers; such containers can be boxes, ampules, bottles, vials, tubes, bags, pouches, blister-packs, or other suitable container form known in the art. Such containers can be made of plastic, glass, laminated paper, metal foil, or other materials suitable for holding nucleic acids.

The components of the kit may, for example, be present in one or more containers, for example, all of the components may be in one container, or, for example, the enzymes may be in a separate container from the primers. The components may, for example, be dried (e.g., powder) or in a stable buffer (e.g., chemically stabilized, thermally stabilized). Dry components may, for example, be prepared by lyophilization, vacuum and centrifugal assisted drying and/or ambient drying. In various embodiments, the polymerase and nicking enzymes are in lyophilized form in a single container, and the primers are either lyophilized, freeze dried, or in buffer, in a different container. In some embodiments, the polymerase, nicking enzymes, and the primers are, in lyophilized form, in a single container. In other embodiments, the polymerase and the nicking enzyme may be separated into different containers.

Kits may further comprise, for example, dNTPs used in the reaction, or modified nucleotides, cuvettes or other containers used for the reaction, or a vial of water or buffer for re-hydrating lyophilized components. The buffer used may, for example, be appropriate for both polymerase and nicking enzyme activity.

The kits of the present invention may also comprise instructions for performing one or more methods described herein and/or a description of one or more compositions or reagents described herein. Instructions and/or descriptions may be in printed form and may be included in a kit insert. A kit also may include a written description of an Internet location that provides such instructions or descriptions.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1. A Nicking and Extension Reaction Substrate with Detectable Reporter that can be Used as an Exogenous/Internal Control Molecule The present invention provides a nicking and extension reaction substrate that is an oligonucleotide duplex having a nick site on one strand that is 5' to a detectable fluorescent reporter molecule that is covalently linked at the 3' end of the strand (FIGS. 1A and 1B). A quencher at the 5' end of the opposite strand prevents the reporter molecule from fluorescing (FIGS. 1A and 1B). When the substrate molecule is nicked, the resulting internal 3' end can be extended by polymerase, using the opposite strand as template (FIGS. 1C-1E). Polymerase extension results in displacement of the portion of the strand linked to the fluorescent reporter (FIG. 1E). When the fluorescent reporter is separated from the quencher, it generates a fluorescent signal (FIG. 1E). Additional improvements can be made to the substrate molecule to prevent or minimize further rounds of nicking and extension (FIG. 1F).

Figure 2B:
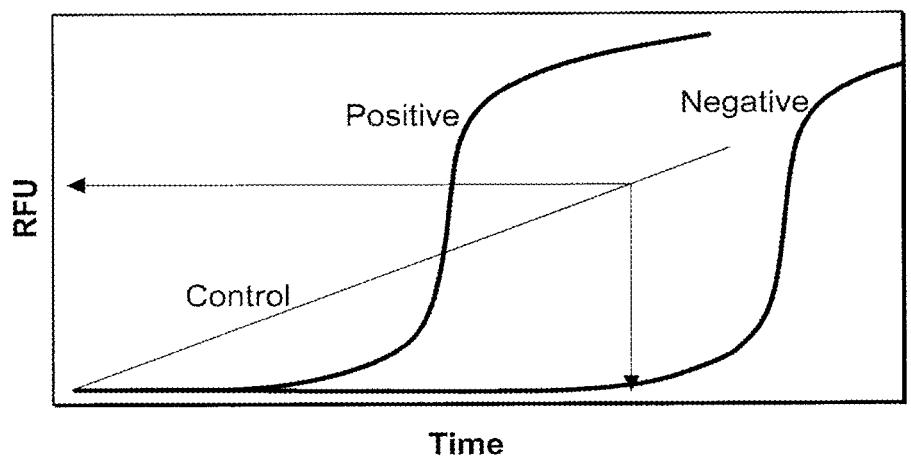

The reaction of the substrate molecule in the presence of a nicking enzyme and polymerase generates a linear signal, particular when the 3' ends of the oligonucleotides are blocked from further interactions (FIG. 2A). The substrate molecule can be added to nicking amplification reactions as an exogenous/internal control to show that a nicking enzyme and polymerase has activity in the reaction. The control reaction and the nicking amplification reaction both start when nicking enzyme and polymerase are active and run in parallel. The control reaction is designed to minimize the use of reaction components, thus minimizing any effects on the amplification reaction Advantageously, reaction end points for a nicking amplification reaction can be set as the time at which the exogenous control molecule reaches a set RFU (FIG. 2B). For example, this may be used to characterize an amplification signal as positive or negative based on its time of detection.

Figure 5A:
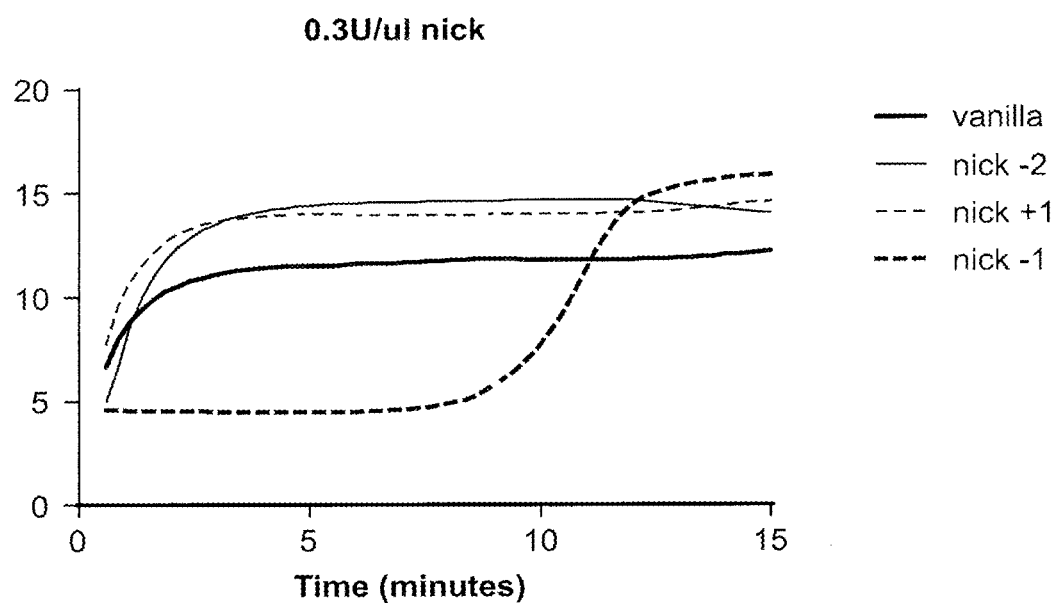
FIGS. 5A-5E depict the activity of the substrate molecules having the oligonucleotide strands described at FIG. 4 in the presence of nicking enzyme, at varying concentration, and polymerase. The results show that the reaction of the substrate molecule can be tuned using modified nucleotides, the concentration of the substrate molecule relative to the amount of nickase, and/or the mixtures of differently modified substrate molecules.
Figure 5B:
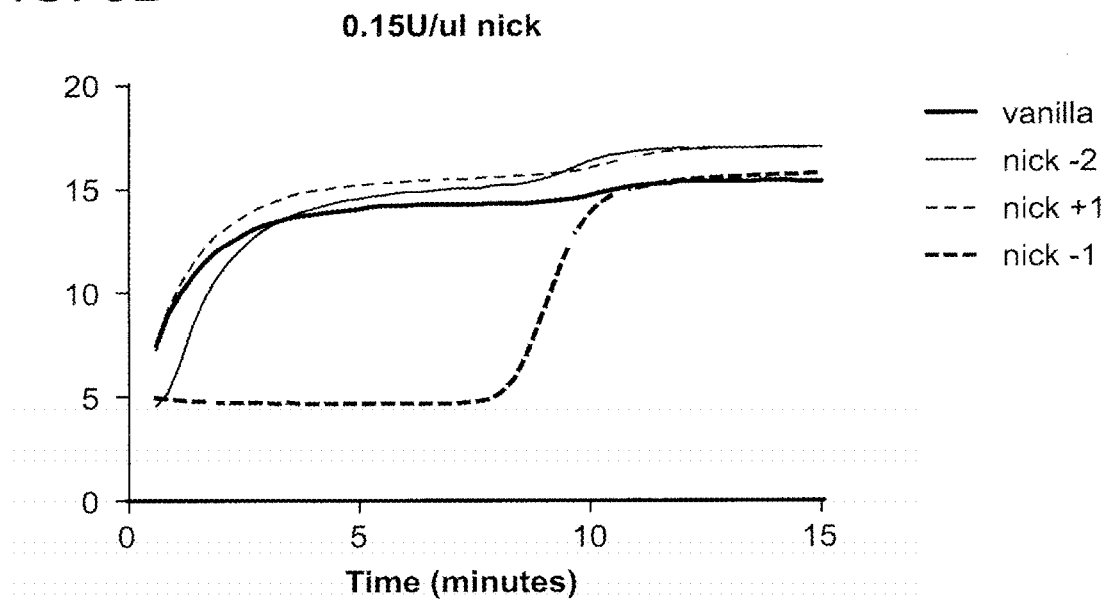
Figure 5C:
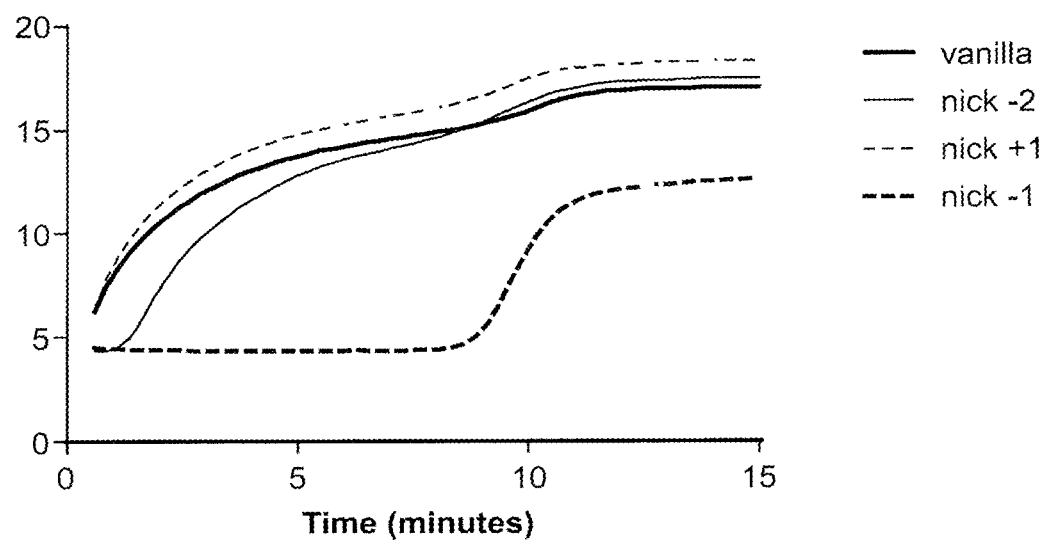
Figure 5D:
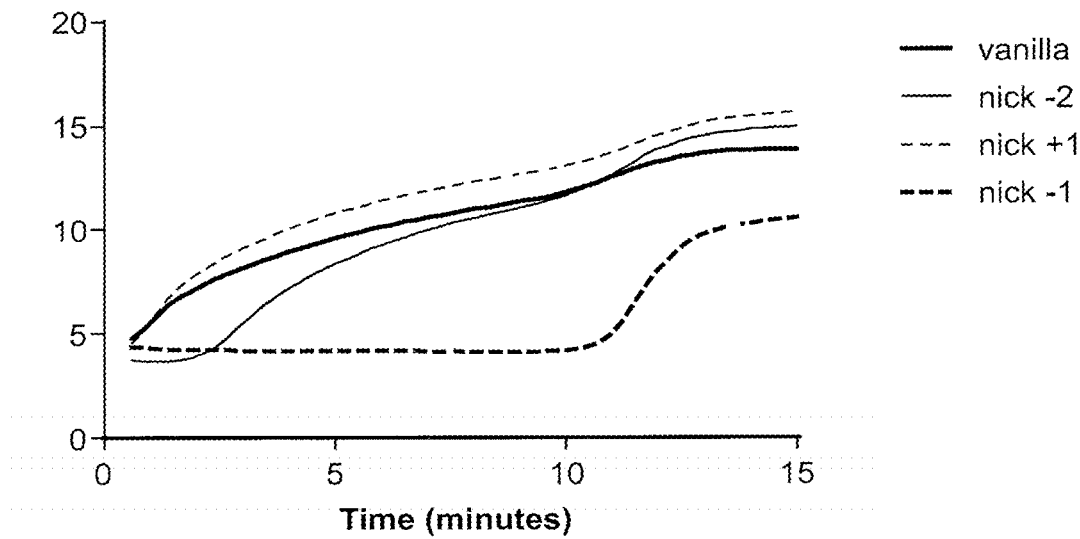
Figure 5E:
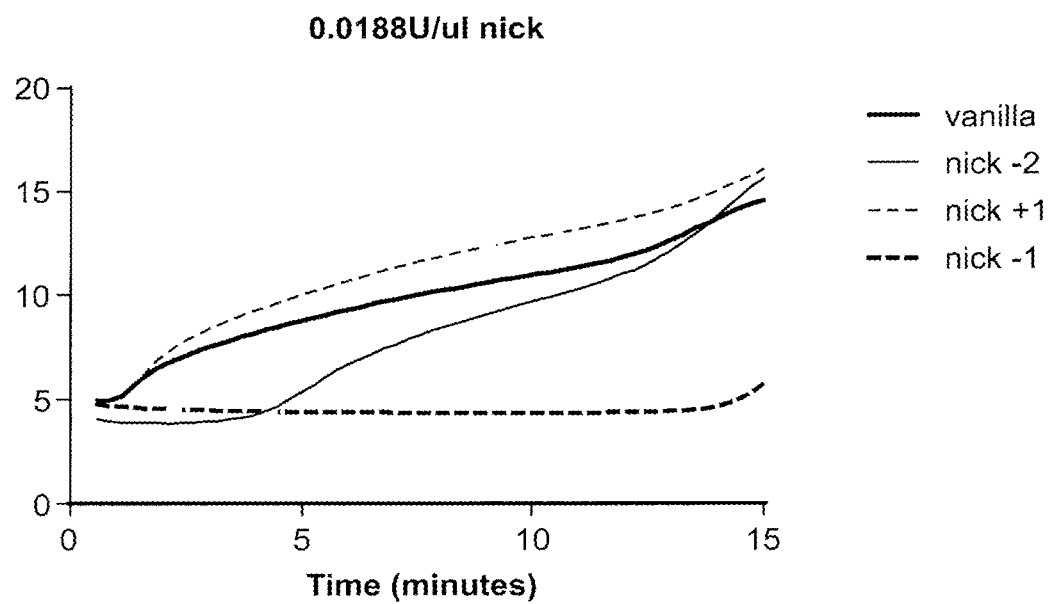
Figure 6A:
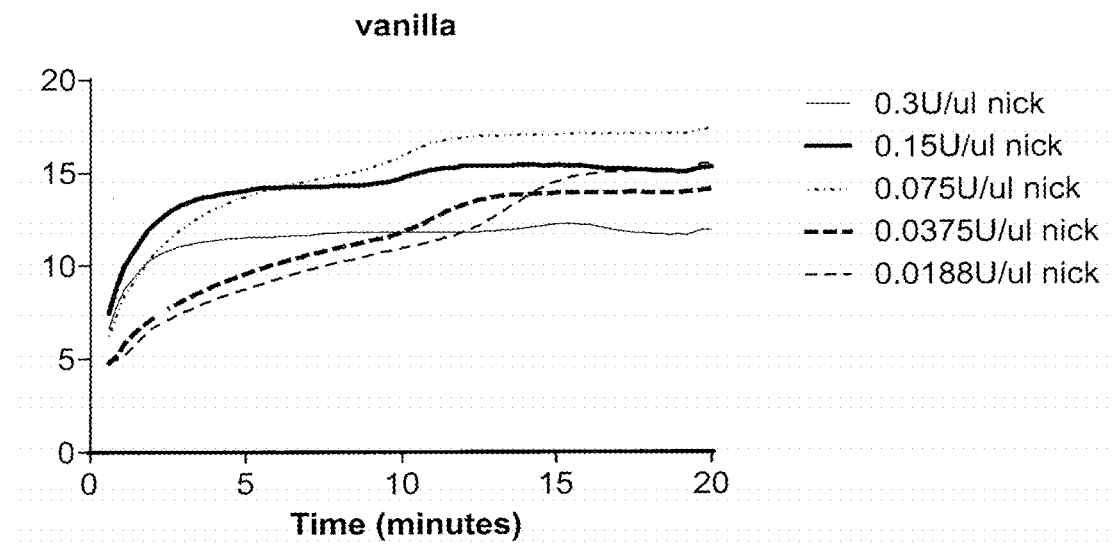
FIGS. 6A-6D depict the graphs shown in FIGS. 4A-4E organized by the unmodified and modified oligonucleotide strands having 3' fluorophore 36-FAM.
Figure 6B:
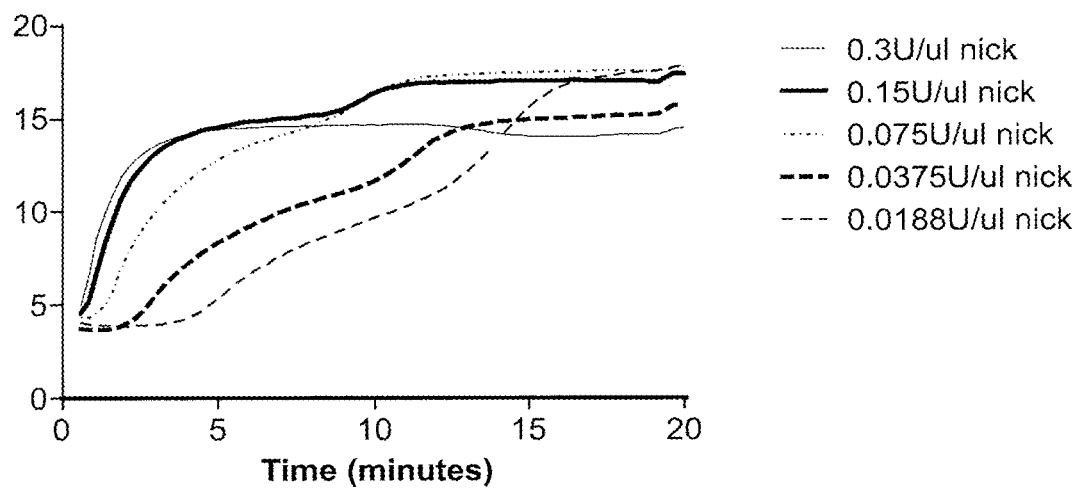
Figure 6C:
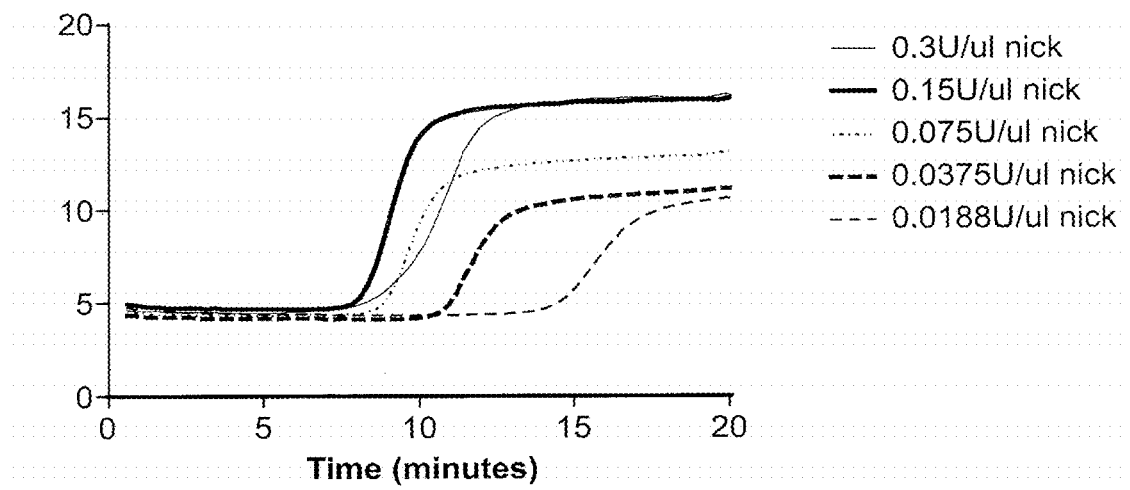
Figure 6D:
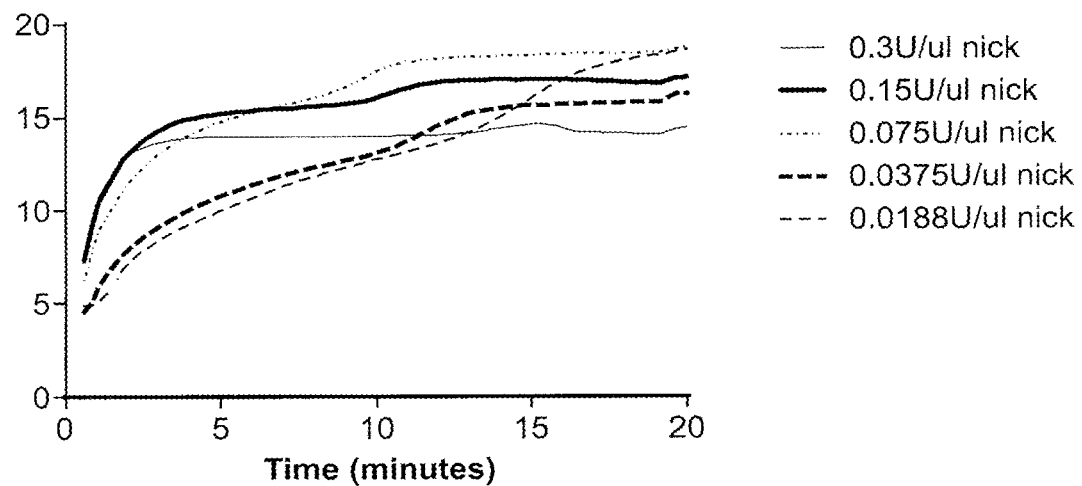

Studies were performed on several substrate molecules having modified nucleotides at various positions surrounding the nick site (FIG. 4). For these studies, the 3' end of the oligonucleotide having the quencher was not blocked. The substrate molecules showed the expected reaction profile. A fast linear response was observed at relatively high concentrations of nicking enzyme, in most cases with maximum RFU quickly reached in under 5 minutes (FIGS. 5A-5E and 6A-6D). In particular, the nick −1 substrate molecule having a 2'OMe at the first position 5' of the nick site showed a delayed response compared to the other substrate molecules (FIG. 6C). At relatively lower concentrations of nicking enzyme, the time to maximum RFU could be extended (FIGS. 5D and 5E).

Changes were made to the length of the portion of the oligonucleotide 5' of the GAGTC nicking enzyme recognition site (FIG. 7). The top strands A, B, C all have equivalent activities based on slope. The reaction curve of top strand D, which has two nucleotides 5' of the nicking enzyme recognition site, begins to change slightly. A further decrease in the reaction response is observed in top strand E, which has which has one nucleotide 5' of the nicking enzyme recognition site. No reaction was observed for top strand F, which has no nucleotides 5' of the nicking enzyme recognition site. Thus, these data show full activity of the nicking enzyme, when there are three or more nucleotides to the 5' side of the GAGTC nick recognition site. The difference in activities provides choice of reaction rates so that the exogenous control will be compatible with different assays.

Example 2. Tunability of the Exogenous Control Reaction

Figure 8:
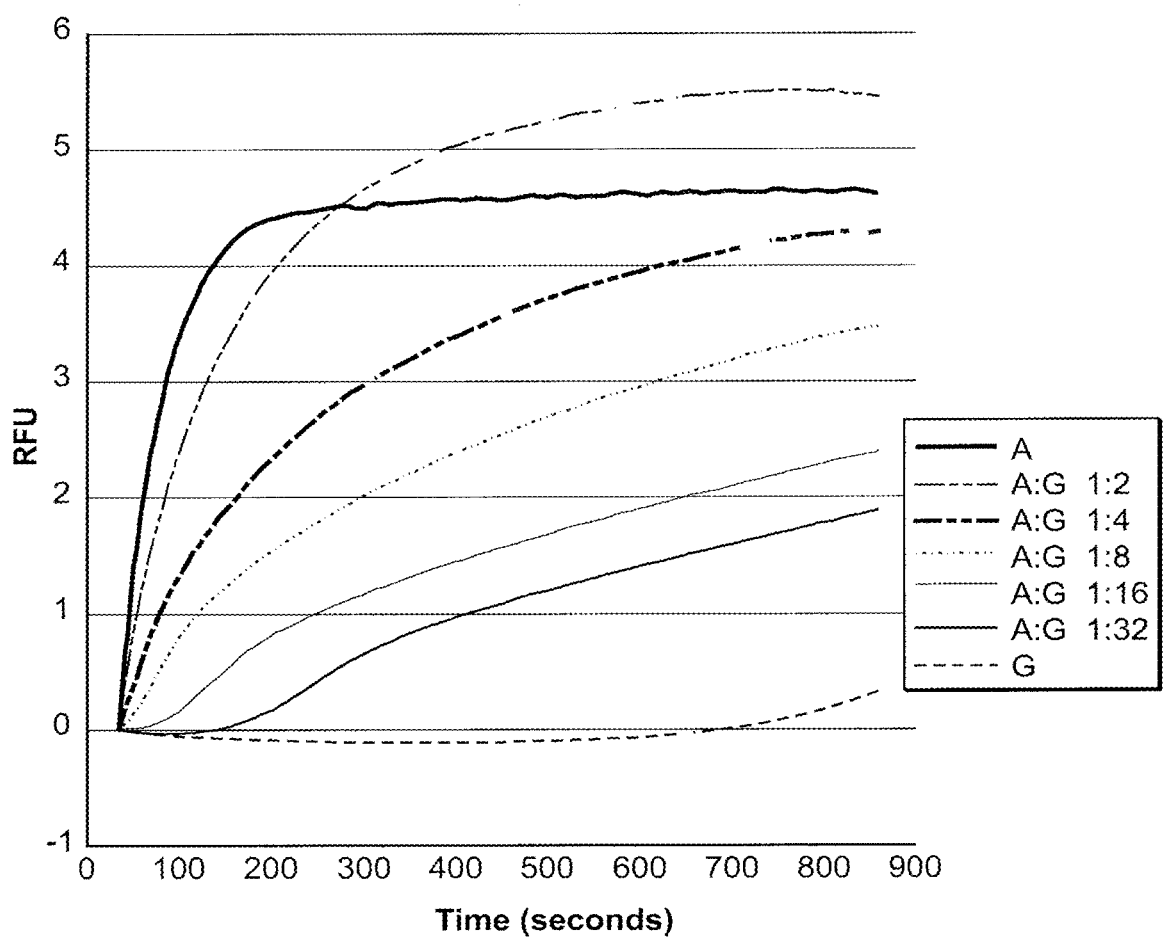
FIG. 8 depicts the results of a study to determine the effect of using different ratios of substrate molecules comprising unmodified and modified nucleotides. A graph of the reaction curves is shown for reactions having the specified ratios of substrate molecules. Sequences of the oligonucleotide strands of the unmodified and 2'OMe modified substrate molecules are shown below the graph. This shows that the reaction can be tuned to reach a desired threshold at a prespecified time by using different ratios of different substrate molecules.

In one aspect of the invention, the exogenous control reaction can be tuned, which allows customization of the exogenous control reaction to be run under a given set of nicking amplification reaction conditions. Using different ratios of substrate molecules comprising unmodified and modified nucleotides, the reaction rate can be controlled (FIG. 8). The non-modified top strand (A) was titrated with the double methoxy modified oligonucleotide (G). With added amounts of the modified oligonucleotide, the reaction rate (slope) was controlled, and could be tuned to reach a desired threshold at a prespecified time. These results show that mixtures of the exogenous control molecule can be used as a 'reaction timer' as well as a positive reaction control.

Figure 9A:
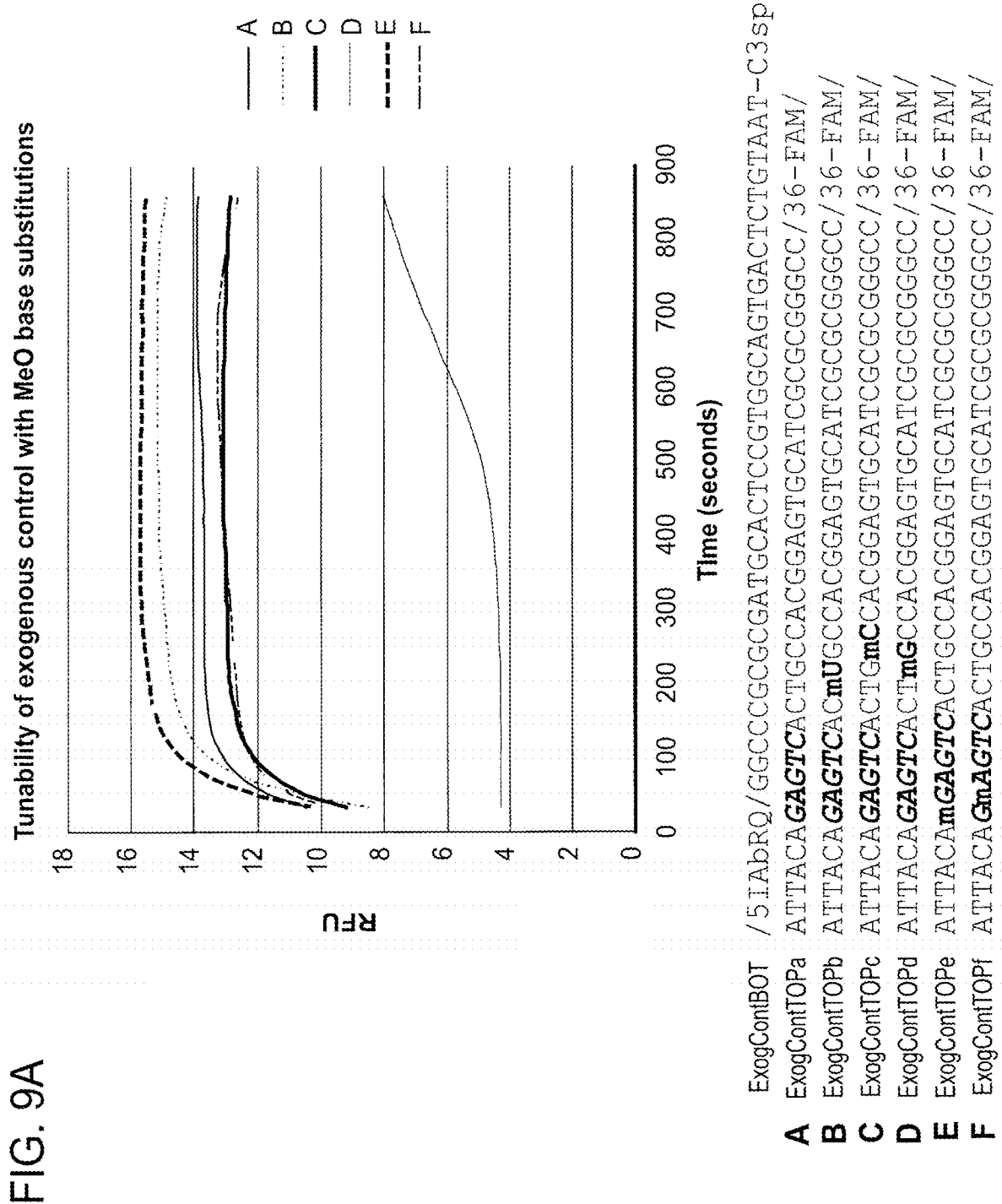
FIGS. 9A and 9B depicts the results of a study to determine the effect of positioning modified nucleotides at various positions within the substrate molecule.
Figure 9B:
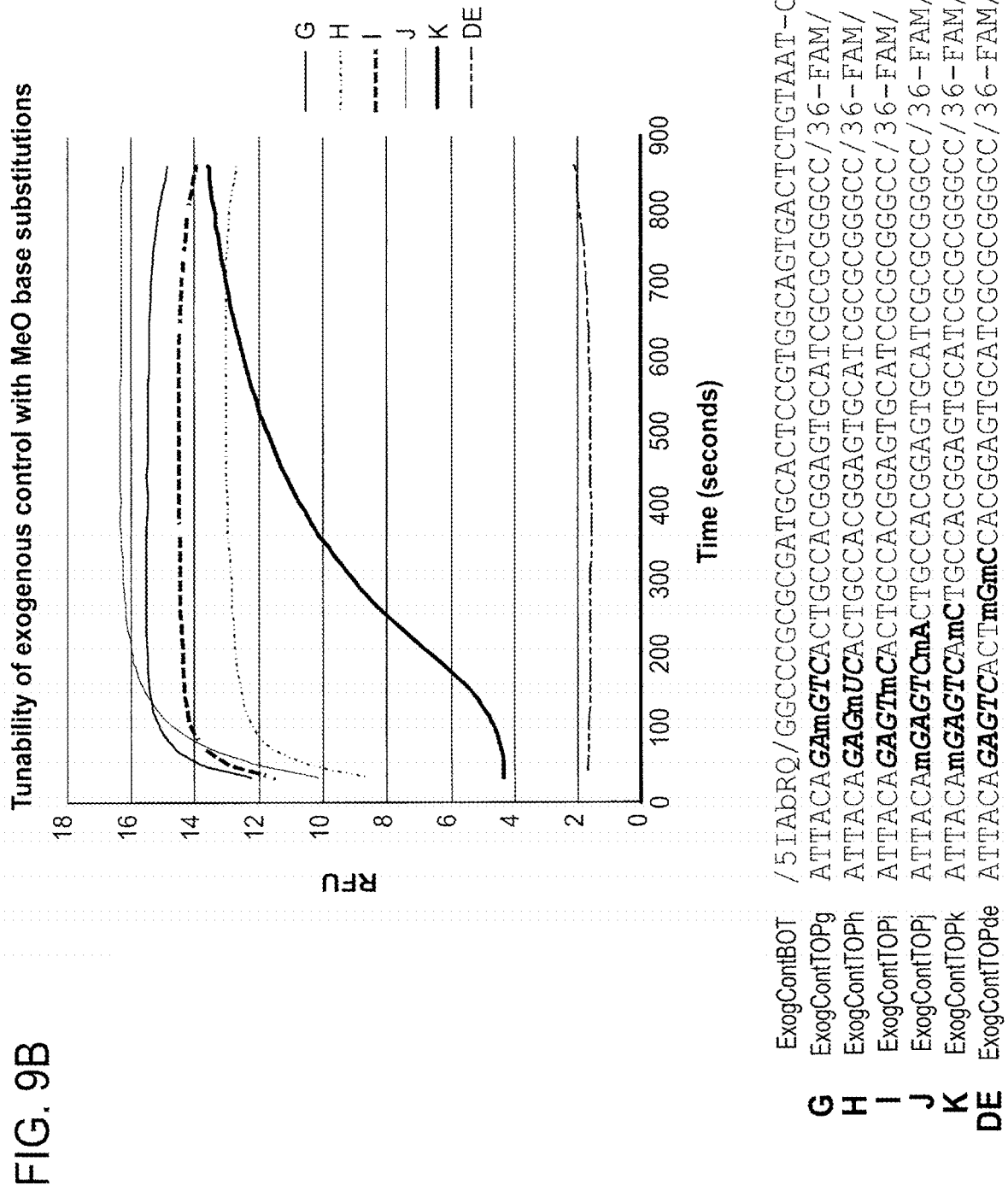

In another aspect, the exogenous control reaction can be tuned by positioning 2'OMe modified nucleotides at various positions within the substrate molecule in proximity to the nick site and nicking enzyme recognition site (FIGS. 9A and 9B). Modified top strands (A-K and DE) were used in combination with a bottom strand blocked with a C3 spacer. Relatively equivalent results with all but top strand D which is at the 'nick −1' (last 5' base before Nt.BstNBI nick site). Previous results also showed a small effect from top strand B using less nicking enzyme. Relatively equivalent results were observed with all 2'OMe modified nucleotides placed in the nicking recognition site (GAGTC). The most noticeable effect was seen when 2'OMe modified nucleotides were placed on either side of the nick site.

Figure 10:
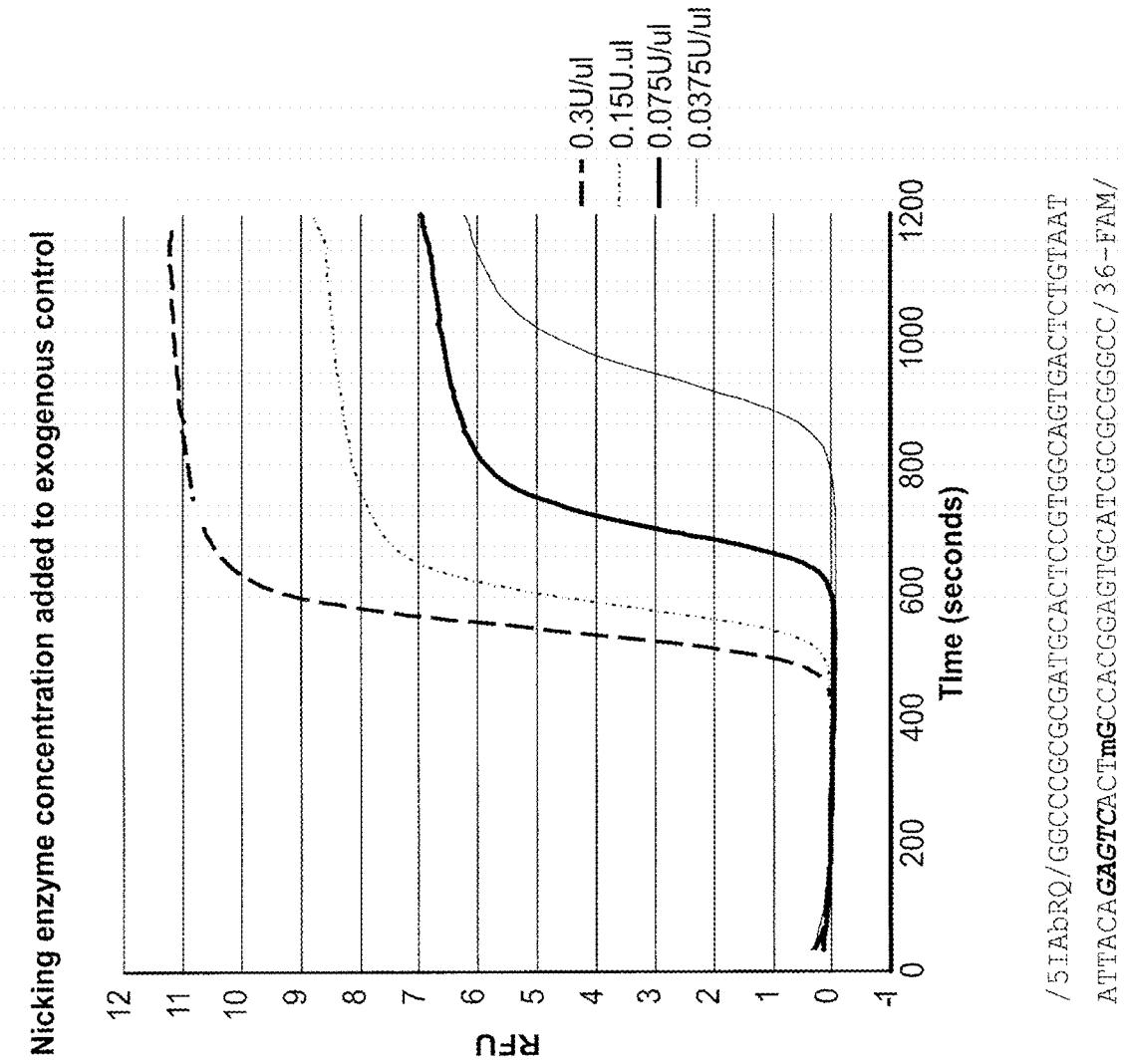
FIG. 10 depicts the results of a study showing that the substrate molecule can be used to test nicking enzyme and/or polymerase.
Figure 11:
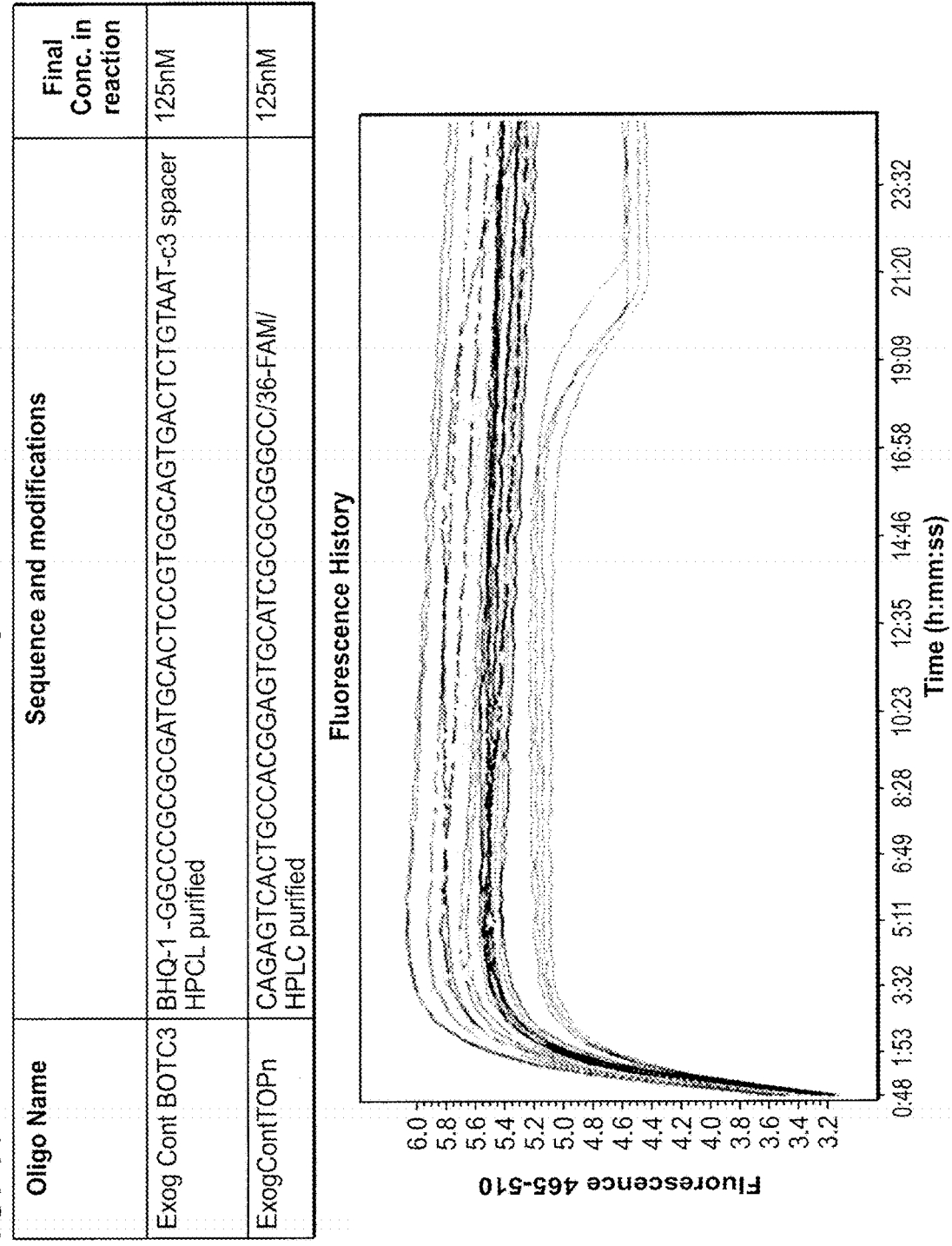
FIG. 11 depicts finalized sequences for an exogenous/internal control molecule for use with a *Salmonella* assay based on a nicking amplification reaction.

Example 3. Using the Nicking and Extension Reaction Substrate for Assaying Nicking Enzyme and Polymerase Activity In one aspect of the invention, the substrate molecule can be used to test reaction conditions to determine the activities of combinations of nicking enzymes and polymerases and characterizing their composite activity. Due to differences in the properties (e.g., thermal properties) of nicking enzymes and polymerases, there is potential for optimizing reaction conditions to maximize overall nicking and extension reaction activity. Prior to the present invention, such an analysis was unavailable. The modified top strand is used in conjunction with an unblocked bottom strand (unblocked 3' end). Nicking enzyme and/or polymerase can be tested for activity with these oligonucleotides to provide a very controlled reaction with high replicability while still mimicking a true amplification reaction in terms of enzyme function. Either blocked or unblocked 3' ends can be utilized depending on the desired readout. A study was performed showing the effect of nicking enzyme concentration on the reaction of the substrate molecule (FIG. 10).

Example 4. Test Kit for Qualitative Detection of DNA from *Salmonella*, Including Exogenous/Internal Control Rapid, point of need detection of *Salmonella* is required to effect interventions to prevent its spread. A test kit was generated for qualitative detection of DNA from *Salmonella*. The detection assay is based on an isothermal nucleic acid amplification method. The kit also includes an exogenous/internal control to confirm the activities of the nicking enzyme and polymerase in each reaction. To optimize the assay a list of primers and beacon sequences was tested first. The following primers were used for amplification of the target nucleic acid molecule.

```
Forward Primers
5'-TGACTCCATATGGAGTCACATCACmCGAAATACmCmGmCmCmA-3'

5'-GACTCGATATCGAGTCTTTCCACmCGAAATACmCmGmCmCmA-3'*

5'-GAAAGACTCGCGAGTCTTTCCACmCGAAATACmCmGmCmCmA-3'

Reverse Primers
5'-TGACTCCATATGGAGTCACATCGGmCATCATTATTATCTTTGmUmGm
AmAmC-3'

5'-GACTCGATATCGAGTCTTTCCGGmCATCATTATTATCTTTGmUmGmA
mAmC-3'*

5'-GAAAGACTCGCGAGTCTTTCCGGmCATCATTATTATCTTTGmUmGmA
mAmC-3'
```

Bases labeled with the prefix "m" indicate the position of 2'-O-methyl ribonucleotides.
The following probe was used for detection of the target nucleic acid molecule:
"Molecular Beacon" Detection Probe

```
5'-CalRed_{610nm}-CGCCTGTGAACTTTATTGGCG-BHQ2-3'
```

The duplex of the following oligonucleotides were used as an exogenous and internal control (FIG. 11):
Exogenous Control Bottom (BOT) 3 Carbon Spacer (C3-Spacer):

```
5' Black Hole Quencher (BHQ)-1
GGCCCGCGCGATGCACTCCGTGGCAGTGACTCTGTAAT-c3 spacer 3'
```

HPLC purified
Exogenous Control Top (Topn):

```
5' CAGAGTCACTGCCACGGAGTGCATCGCGCGGGCC/36-FAM/3'
```

HPLC purified

The above primers and probes were tested in isothermal nucleic acid amplification reactions. Test samples were prepared from simulated pet food or enriched culture. The amplification and detection reactions displayed a high signal to noise ratio, early onset of exponential amplification, steep amplification slope, rapid time to detection, and low signal variance among replicated assay reactions. All target control samples showed robust signal. The exogenous/internal control provided a means of detecting the activity of the nicking enzyme and polymerase while minimizing interference with the isothermal nucleic acid amplification reactions. The assay was further tested and detected a list of over 100 *Salmonella* serotypes. These results indicate that the foregoing reaction and reagents can be used for rapid, accurate detection of *Salmonella*.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of detecting nicking enzyme and polymerase activity in a reaction in real time comprising:
   a) contacting a nucleic acid duplex with a nicking enzyme, wherein the nucleic acid duplex is nicked by the nicking enzyme, the duplex comprising:
      i) a first nucleic acid strand comprising a nicking enzyme recognition site, a nick site, and a fluorescent detectable label covalently linked at the 3' end; and
      ii) a second nucleic acid strand having a sequence capable of duplexing with the first strand and a quencher moiety at the 5' end;
      or
      i) a first nucleic acid strand comprising a nicking enzyme recognition site, a nick site, and a quencher moiety covalently linked at the 3' end; and
      ii) a second nucleic acid strand having a sequence capable of duplexing with the first strand and a fluorescent detectable label covalently linked at the 5' end;
   b) contacting the nicked duplex with a polymerase in the presence of dNTPs;
   c) extending the nicked duplex with the polymerase, thereby displacing the portion of the first nucleic acid strand 3' of the nick site covalently linked to the fluorescent detectable label or quencher moiety; and
   d) detecting a signal in real time from the fluorescent detectable label that is separated from the quencher, thereby detecting nicking enzyme and polymerase activity in the reaction;
   wherein the first nucleic acid strand is modified at one or more nucleotides between the nicking enzyme recognition site and the nick site, within the nicking enzyme recognition site, within 2, 3, 4 or 5 nucleotides of the nick site (5' or 3'), and/or at position 1 on either side of the nick site (5' and 3').

2. A method of monitoring the amplification of a specific product in a nicking amplification reaction in real time, the method comprising:
   a) contacting a target nucleic acid molecule under substantially isothermal conditions with two or more primers, each of which specifically binds to a target nucleic acid molecule, in the presence of a polymerase, dNTPs, a nicking enzyme, and a duplex comprising:

i) a first nucleic acid strand comprising a nicking enzyme recognition site, a nick site, and a fluorescent detectable label covalently linked at the 3' end; and ii) a second nucleic acid strand having a sequence capable of duplexing with the first strand and a quencher moiety at the 5' end;

or i) a first nucleic acid strand comprising a nicking enzyme recognition site, a nick site, and a quencher moiety covalently linked at the 3' end; and ii) a second nucleic acid strand having a sequence capable of duplexing with the first strand and a fluorescent detectable label covalently linked at the 5' end;

b) generating amplicons comprising at least a portion of said target nucleic acid molecule;

c) nicking the duplex and extending the duplex with the polymerase, thereby displacing the portion of the first nucleic acid strand 3' of the nick site covalently linked to the fluorescent detectable label or quencher moiety; and d) detecting a signal in real time from the fluorescent detectable label that is separated from the quencher, thereby monitoring nicking enzyme and polymerase activity in the reaction;

wherein the first nucleic acid strand is modified at one or more nucleotides between the nicking enzyme recognition site and the nick site, within the nicking enzyme recognition site, within 2, 3, 4 or 5 nucleotides of the nick site (5' or 3'), and/or at position 1 on either side of the nick site (5' and 3').

3. The method of claim 2, further comprising contacting the nucleic acid molecule with two or more primers in the presence of a detectable polynucleotide probe; and e) detecting a signal in real time specific for oligonucleotide probe hybridization to the target nucleic acid molecule or amplicon thereof, wherein the signal indicates the quantity of the target nucleic acid molecule present in the sample or an amplicon thereof.

4. The method of claim 2, wherein the detection of a signal from the duplex is used as a positive control.

5. The method of claim 2, wherein the end point of monitoring the nicking amplification reaction is indicated when the signal from the duplex reaches a set relative fluorescence unit (RFU).

6. The method of claim 1, wherein the reaction is performed under substantially isothermal conditions.

7. The method of 1, wherein the reaction further comprises primers, probe, and/or target nucleic acid molecules.

8. The method of claim 1, wherein the nucleic acid strands have sequences that do not bind to other nucleic acid molecules present in the reaction.

9. The method of claim 3, wherein the detectable polynucleotide probe comprises a fluorescent detectable label, and wherein the fluorescent detectable label of the nucleic acid duplex and the fluorescent detectable label of the probe are different.

10. The method of claim 1, wherein the fluorescent detectable label covalently linked to the first nucleic acid strand is FAM, TET, HEX, TAMRA, JOE, or ROX.

11. The method of claim 1, wherein the quencher moiety covalently linked to the second nucleic acid strand is a 5' dark quencher dye with an orange-red absorbance visual spectral range, dabcyl, dabsyl, or a dark quencher dye with an absorbance range across the visible spectrum.

12. The method of claim 1, wherein the 3' end of the second nucleic acid strand is modified with a C3 spacer, dideoxy nucleotide, phosphorylation, dye, fluorophore, quencher, spacer, or linker.

13. The method of claim 1, wherein the nucleic acid duplex comprises one or more modified nucleotides.

14. The method of claim 13, wherein the one or more modified nucleotides comprises a 2'-O-methyl, 2'-methoxyethoxy, 2'-fluoro, 2'-hydroxyl (RNA), 2'-allyl, 2'-O-[2-(methylamino)-29-oxoethyl], 4'-thio, 4'-CH$_2$-O-2'-bridge, 4'-(CH$_2$)2-O-2'-bridge, and 2'-O-(N-methylcarbamate), methylation, biotinylation, nucleotide adduct, or a base analog.

15. The method of claim 1, wherein the nicking enzyme is Nt.BstNBI, N.Bst9I, N.BstSEI, Nb.BbvCI, Nb.Bpu10I, Nb.BsmI, Nb.BsrDI, Nb.BtsI, Nt.AlwI, Nt.BbvCI, Nt.Bpu10I, Nt.BsmAI, Nt.BspD6I, Nt.BspQI, or Nt.CviPII.

16. The method of claim 1, wherein the polymerase is Bst DNA polymerase I, Bsu DNA polymerase, Gst DNA polymerase I, or Gka DNA polymerase I.

17. The method of claim 1, wherein the nucleic acid duplex is between about 30 bp to about 2 kb in length, between about 100 bp to about 1 kb in length, between about 100 to about 500 bp in length, between about 30 to about 200 bp in length, between about 30 to about 60 bp in length, between about 35 to about 50 bp in length.

18. The method of claim 1, wherein the nucleic acid strands are between about 30 to about 2000 nt in length, between about 100 to about 1000 nt in length, between about 100 to about 500 nt in length, between about 30 to about 100 nt in length, between about 30 to about 60 nt in length, between about 35 to about 50 nt in length.

19. The method of claim 1, wherein the length of the nucleic acid strand 3' of the nick site is about 25 nt, about 35 nt, about 40 nt or more.

20. The method of claim 1, wherein the length of the nucleic acid strand 5' of the nick site is 10 nt, about 15 nt, about 20 nt or more.

21. The method of claim 1, wherein the length of the nucleic acid strand 5' of the nicking enzyme recognition site is about 10 nt, about 5 nt, about 3 nt or less.

22. The method of claim 1, wherein the length of the nucleic acid strand 5' of the nicking enzyme recognition site is 4, 3, 2, or 1 nt.

23. The method of claim 1, wherein the first and second nucleic acid strands are covalently linked.

24. The method of claim 12, comprising the use of one or more nucleic acid duplexes that differ in their modification.

25. The method of claim 2, wherein the target nucleic acid molecule is obtained from a test sample.

26. The method of claim 25, wherein the test sample comprises a pathogen.

27. The method of claim 25, wherein the test sample is a biological sample.

28. The method of claim 27, wherein the biological sample is a biological fluid, cell, or tissue sample.

29. The method of claim 28, wherein the biological fluid is saliva, sweat, tears, fluids accumulating in a bodily cavity, urine, ejaculate, vaginal secretion, cerebrospinal fluid, lymph, feces, sputum, decomposition fluid, vomit, sweat, breast milk, blood, serum, or plasma.

30. The method of claim 25, wherein the test sample is an environmental sample.

* * * * *